United States Patent
Leysen et al.

(10) Patent No.: US 9,126,933 B2
(45) Date of Patent: Sep. 8, 2015

(54) SOFT PDE4 INHIBITORS

(75) Inventors: Dirk Leysen, Diepenbeek (BE); Olivier Defert, Diepenbeek (BE); Sandro Boland, Diepenbeek (BE)

(73) Assignee: Amakem NV, Diepenbeek (BE)

(*) Notice: Subject to any disclaimer, the term of this patent is extended or adjusted under 35 U.S.C. 154(b) by 0 days.

(21) Appl. No.: 14/237,381

(22) PCT Filed: Aug. 9, 2012

(86) PCT No.: PCT/EP2012/065555
§ 371 (c)(1),
(2), (4) Date: Feb. 6, 2014

(87) PCT Pub. No.: WO2013/021021
PCT Pub. Date: Feb. 14, 2013

(65) Prior Publication Data
US 2014/0187555 A1    Jul. 3, 2014

(30) Foreign Application Priority Data
Aug. 9, 2011    (GB) .................................. 1113689.2

(51) Int. Cl.
C07D 213/04    (2006.01)
C07D 213/75    (2006.01)
C07D 401/12    (2006.01)
C07D 405/12    (2006.01)

(52) U.S. Cl.
CPC ............ C07D 213/04 (2013.01); C07D 213/75 (2013.01); C07D 401/12 (2013.01); C07D 405/12 (2013.01)

(58) Field of Classification Search
None
See application file for complete search history.

(56) References Cited

U.S. PATENT DOCUMENTS

| | | | |
|---|---|---|---|
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |

FOREIGN PATENT DOCUMENTS

| | | |
|---|---|---|
| WO | 9509615 A1 | 4/1995 |
| WO | 9703967 A1 | 2/1997 |
| WO | 2006117653 A1 | 11/2006 |

OTHER PUBLICATIONS

Boswell-Smith et al., "PDE4 inhibitors as potential therapeutic agents in the treatment of COPD-focus on roflumilast", International Journal of COPD 2(2), pp. 121-129, 2007.
Pages et al., "PDE4 inhibitors: a review of current developments (2005-2009)", Expert Opinion on Therapeutic Patents, Informa Healthcare, GB, vol. 19, No. 11, pp. 1501-1519, Jan. 1, 2009.
Press et al., "2 PDE4 Inhibitors—A review of the Current Field", Progress in Medicinal Chemistry, vol. 47, pp. 37-74, Jan. 1, 2009.
Search Report for International Application No. PCT/EP2012/0655555 dated Nov. 5, 2012.
International Preliminary Report on Patentability for International Application No. PCT/EP2012/0655555 dated Dec. 20, 2013.

*Primary Examiner* — Timothy R Rozof
(74) *Attorney, Agent, or Firm* — Dinsmore & Shohl LLP

(57) ABSTRACT

The present invention relates to new phosphodiesterase inhibitors, more specifically soft PDE4 inhibitors, compositions, in particular pharmaceuticals, comprising such inhibitors, and to uses of such inhibitors in the treatment and prophylaxis of disease. In particular, the present invention relates to new soft PDE4 inhibitors compositions, in particular pharmaceuticals, comprising such inhibitors, and to uses of such inhibitors in the treatment and prophylaxis of disease. In addition, the invention relates to methods of treatment and use of said compounds in the manufacture of a medicament for the application to a number of therapeutic indications including inflammatory diseases.

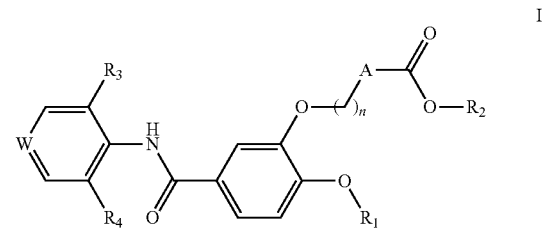

16 Claims, No Drawings

SOFT PDE4 INHIBITORS

FIELD OF THE INVENTION

The present invention relates to new, soft phosphodiesterase inhibitors, more specifically soft PDE4 inhibitors, compositions, in particular pharmaceuticals, comprising such inhibitors, and to uses of such inhibitors in the treatment and prophylaxis of disease. In particular, the present invention relates to new soft PDE4 inhibitors compositions, in particular pharmaceuticals, comprising such inhibitors, and to uses of such inhibitors in the treatment and prophylaxis of disease.

In addition, the invention relates to methods of treatment and use of said compounds in the manufacture of a medicament for the application to a number of therapeutic indications including inflammatory diseases.

BACKGROUND OF THE INVENTION

Cyclic nucleotide phosphodiesterase (PDE) enzymes are a superfamily of intracellular enzymes. In humans, 21 PDE genes are known, belonging to 11 PDE families. However, many more than 21 mRNA and protein products are known to be transcribed from these 21 genes, as alternative transcriptional start sites and alternative splicing of mRNA precursor molecules exist. Hence, the 11 PDE families encompass over 60 isoforms.

PDEs degrade cyclic nucleotides, in particular cyclic adenosine 3',5'-monophosphate (cAMP) and cyclic guanosine 3',5'-monophosphate (cGMP). cAMP and cGMP are intracellular second messengers playing a key role in mediating cellular responses to various hormones and neurotransmitters. The levels of cAMP and cGMP are tightly regulated by their synthesis (by the enzymes adenylate and guanylate cyclase) as well as their degradadtion (by the PDEs). PDEs render the ability to generate and shape cAMP or cGMP gradients within the cell.

The 11 different PDE families have different affinities for cAMP and cGMP, and each family is therefore involved in the degradation of one or both of these cyclic nucleotides. Any single cell type can express several different PDEs and the nature and intracellular localization of these PDEs is an important regulator of local concentrations of cAMP and cGMP within the cell. The regulation of intracellular cyclic nucleotide levels by PDEs is a complex interplay between the multiple PDE isoforms. Although there may be some redundancy between the different PDE isoforms, it is known that most of the different PDE isoforms have specific physiological roles.

The 11 PDE families are named PDE1 through PDE11, the number referring to the particular gene family. To indicate the gene within the family, a capital letter can be added to this name. Further numbers specifying the variant can then be further added to the name. Furthermore, often a species code is added preceding the name, e.g. Hs stands for *Homo sapiens*. An example of a PDE name according to this nomenclature would be HsPDE1A2. In an alternative annotation system, PDEs are written in lower case italic letters when referring to a gene, and in non italicized capital letters when referring to a protein, and a letter "v" is added preceding the variant number. An example of a PDE gene name and the corresponding PDE protein name according to this nomenclature would be Pde1a_v2 and PDE1A_V2, respectively.

When analyzing crystallographic data, PDE catalytic domains have been found to consist of a compact arrangement of 16 α-helices arranged in three subdomains. The active site is located at the intersection of these three subdomains. Of the 16 invariant amino acids across the 21 PDE genes, 11 are located in the active site. Two metal ions, in particular magnesium and/or zinc, are coordinated each by six residues found at the bottom of the active site. These residues are located on each of the three subdomains. As two metal ions are needed, a binuclear catalytic mechanism for cleaving the cyclic phosphate group of cAMP or cGMP has been suggested. To accommodate the substrate, conserved aromatic residues at the roof of the active site enable a stacking arrangement with the cyclic nucleotide, a hydrophobic residue at the bottom of the active site enables hydrophobic interaction, and further hydrogen bonds are formed with the conserved active site glutamine, finally the phosphate group interacts with the two metal ions directly or via a water molecule. The conserved active site glutamine, which is also named glutamine switch, is a key determinant of cyclic nucleotide specificity. The glutamine switch stabilizes the binding of the cyclic nucleotide purine ring in the active site. To accommodate the binding of both cAMP and cGMP, free rotation of this conserved glutamine residue is required. In PDEs which are selective for one of the cyclic nucleotides, the free rotation of the conserved glutamine residue is constrained by neighboring residues into an orientation favoring cAMP binding only, or into an orientation favoring cGMP binding only.

The PDE4 family, encoded by four genes (PDE4A, PDE4B, PDE4C, and PDE4D) and containing over 20 identified isoforms, is the largest of the 11 PDE families. PDE4 is a cAMP-specific phosphodiesterase, hence its original name cAMP-PDE. PDE4 isoforms are distributed widely and can be found in most tissues and cell types, including the airways smooth muscle, brain, and cardiovascular tissues. Therefore, PDE4 inhibitors may target multiple cell types. Most PDE4 isoforms have tissue- and cell-type-specific expression. As PDE4 isoforms arise from differences in their N termini, which encode regulatory domains and phosphorylation sites, it will be appreciated that different isoforms are subject to different regulatory mechanisms. PDE4 isoforms have distinct cellular localizations as well.

PDE4 isoforms are omnipresent among proinflammatory and inflammatory cells, and immune cells, and PDE4 is the main cAMP-metabolizing enzyme in these cells. Raising intracellular cAMP levels within inflammatory cells, which can be achieved by inhibiting PDE4 activity, inhibits inflammatory cell function.

Diseases for which PDE4 inhibitors have been developed or are currently being developed include—but are not limited to—chronic obstructive pulmonary disease (COPD), asthma, dry eye disease, arthritis, psoriasis, atopic dermatitis, inflammatory bowel disease, and major depressive disorder. PDE4 inhibitors are also being investigated as memory-enhancing agents. In addition, PDE4 inhibitors are of potential interest for the treatment of fibrotic diseases, including Idiopathic Pulmonary Fibrosis (IPF).

COPD is a respiratory disease characterized by small airway fibrosis, mucus hypersecretion, and emphysema, resulting in a rapid decline in lung function. While the main genetic cause of COPD is α1 anti-trypsin deficiency, cigarette smoking is the major risk factor for COPD development. Inhaled cigarette smoke activates resident cells in the lungs including fibroblasts, epithelial cells, and alveolar macrophages to release cytokines, chemokines, and lipid mediators (including tumor necrosis factor α (TNF-α), interleukin-8 (IL-8), transforming growth factor β (TGF-β), and leukotriene B4 (LTB4)). As a result, inflammatory cells are recruited and activated to release a cocktail of proteases into the matrix compartment. This cocktail of proteases can provoke a complex remodeling process leading to alveolar wall destruction, mucus hypersecretion, and peribronchiolar fibrosis, ultimately resulting in COPD. Moreover, exposure to tobacco smoke can induce an imbalance in the oxidant versus antioxidant ratio in favor of oxidative stress. Inflammation can continue in patients long after smoking cessation. It is appreciated that targeting the inflammation and remodeling processes associated with COPD may slow down disease progression and potentially reverse the decline in lung function. Drugs frequently used to treat COPD include β2 agonists, anticholinergic agents, methylxanthines (such as the PDE inhibitor theophylline), and inhaled glucocorticosteroids. These drugs reduce exacerbations and symptoms of COPD, but may not reduce disease progression. Since the inflammation and remodeling process is driven by a number of mediators with overlapping roles, targeting individual mediators is unlikely to result in any therapeutic benefit. As PDE4 inhibitors can decrease/suppress the release of a wide range of inflammatory mediators, cytokines, chemokines, and proteases from cells implicated in COPD, their use in the treatment of COPD may be advantageous. In the clinic, PDE4 inhibitors, including roflumilast and cilomilast, have shown efficacy in COPD treatment.

Asthma is a chronic inflammatory disease of the airways characterized by variable and recurring symptoms, reversible airflow obstruction, and bronchospasm. Unlike COPD, the airway obstruction in asthma is usually reversible. If left untreated however, the chronic inflammation of the lungs can become irreversible obstruction due to airway remodeling. In contrast to emphysema, asthma affects the bronchi, not the alveoli. Asthma is caused by a combination of genetic and environmental factors. Bronchodilators are recommended for short-term relief of symptoms. Acute symptoms are usually treated with an inhaled short-acting β2 agonist. Inhaled corticosteroids or oral leukotriene antagonists are used for symptom prevention, while also avoidance of triggers might prevent asthma. For severe asthma exacerbation, oral glucocorticoids are added to the treatment. PDE4 inhibitors may have use in the inhibition of inflammatory cells involved in asthma. Moreover, as PDE4 inhibitors have been found to induce relaxation of isolated human bronchus, they might also possess bronchodilator activity, which is beneficial in the treatment of asthma. In the clinic, the PDE4 inhibitor roflumilast has been found to reduce the early asthmatic response to antigen challenge and to suppress the late asthmatic response. The late asthmatic response is viewed to represent the inflammatory component of airway disease. Moreover, roflumilast led to increased forced expiratory volume in 1 second (FEV1) and improved morning and evening peak expiratory flow.

Dry eye is a disease of the tears and the ocular surface, leading to ocular discomfort and blurred vision. The disease can be caused by numerous factors, but once established, inflammation of various ocular tissues propagates the disease as both cause and consequence of ocular surface damage. Artificial tears might improve symptoms, but the relief is temporary as the underlying inflammation persists. Given their anti-inflammatory properties, PDE4 inhibitors might reduce eye inflammation. Moreover, other agents that increase cAMP have been found to induce tear secretion, thus PDE4 inhibitors might induce tear secretion as well. Hence in the treatment of eye disease, PDE4 inhibitors might serve the dual role of inflammation reduction and induction of tear secretion.

In addition to COPD, asthma, and dry eye disease, other inflammatory diseases for which PDE4 inhibitors are being developed include inflammatory bowel disease, psoriasis, atopic dermatitis, and arthritis. These uses are based on the effect of decreased PDE4 activity to reduce inflammatory responses of multiple cell types. PDE4 inhibitors suppress the release of inflammatory mediators and immune cell infiltration, in particular, major dampening effects have been observed on neutrophil, monocyte, and T-lymphocyte function.

PDE4 inhibitors are also of interest for the treatment of fibrotic diseases. Fibrosis is the formation of excess fibrous connective tissue in an organ or tissue in a reparative or reactive process, following injury or long term inflammation. Fibrotic diseases are characterized by the accumulation of extracellular matrix together with distortion and disruption of tissue architecture. Among them, Pulmonary Fibrosis (PF) involves the overgrowth, hardening, and/or scarring of lung tissue due to excess collagen. The most common variation of this disease is Idiopathic (unknown cause) Pulmonary Fibrosis (IPF). IPF patients show decline in gas exchange and reduction in total lung volume. Chronic inflammation is a hallmark of PF, with increased amounts of inflammatory cells both in alveolar space and lung interstitium. Numbers of all inflammatory cells is dramatically increased in Bronchoalveolar lavage fluid (BALF) of PF patients, with boost in neutrophil and lymphocyte counts. While this increase in total BALF cell number is mostly accounted for by macrophages, maximal relative increase is observed for granulocytes and lymphocytes. Those changes are accompanied by elevated expression of cytokines such as TNF-α, IL-1β, IL-6, of growth factors and of matrix metalloproteases. As PDE4 inhibitors can modulate inflammatory cell function, it will be appreciated that such inhibitors are of interest for the treatment of fibrotic diseases such as IPF. Additionally, TGF-β has been shown to play a role in multiple fibrotic diseases, including pulmonary fibrosis, renal fibrosis, cardiac fibrosis and vascular fibrosis. TGF-β can potentially modulate cAMP by altering PGE2 metabolism. As a result of their effect on cAMP degradation, PDE4 inhibitors have been shown to functionally antagonize the profibrotic activity of fibroblasts stimulated by TGF-β1. It will therefore be appreciated that PDE4 inhibitors are of interest for the treatment of TGF-β-driven fibrotic diseases.

The prototypical PDE4 inhibitor is rolipram. This compound was originally developed for the treatment of major depressive disorder. It has been found that elevation of cAMP can enhance noradrenergic neurotransmission in the central nervous system. In the clinic, rolipram has been found to be an effective antidepressant, but its development has been stopped due to side effects. In addition, rolipram has an antipsychotic-like action through inhibition of PDE4 activity, indicating that it may be possible to treat psychiatric disorders by directly modulating PDE4-specific cAMP hydrolysis.

In animal models, treatment with PDE4 inhibitors has been found to enhance several models of learning and memory. This finding might indicate a use of PDE4 inhibitors as memory-enhancing agents and for decreasing the memory loss occurring in various types of neurodegenerative disease, in particular—but not limited to—Alzheimer's disease.

Safety-related issues are a significant challenge in the development of PDE4 inhibitors. Reported side effects or adverse events of PDE4 inhibitors include emesis, nausea, dyspepsia, diarrhea, abdominal pain, and headache. A potential side effect that has been observed in several animal models treated with PDE4 inhibitors, but has not been observed in humans yet, is arteritis. Arteritis is characterized by blood vessel inflammation, hemorrhage, and necrosis, and is considered irreversible in animals. The reported side effects of PDE4 inhibitors take place in the brain, gastrointestinal tract, arteries, or in the whole body due to systemic exposure to PDE4 inhibitors. In particular, one problem with PDE4 inhibitors is their tendency to promote emesis, which is mediated at least in part via actions in the central nervous system. In particular, PDE4 is present in parietal cells and emetic centers. A correlation has been found between the emetic effect of PDE4 inhibitors and the occupancy of the rolipram binding site of PDE4 by these inhibitors, indicating that such side effects are directly related to on-target activity. Hence, it will be appreciated that it is difficult to separate the effects on emesis from more desirable effects on the pathology to be treated.

Many development programs of PDE4 inhibitors have been discontinued due to side effects. The full potential of PDE4 inhibitors may not be realized as the administered dose is limited by side effects. Many dose-limiting side effects reflect an adverse interaction of the compound with PDE4 expressed in non-target tissues. In other words, adverse effects of PDE4 inhibitors may be directly related to on-target activity. Hence it will be appreciated that systemic exposure to PDE4 inhibitors should preferably be avoided if not required by the pathology to be treated.

Local application is a first possibility to reduce systemic exposure to a drug compound, by directly delivering the drug compound to the intended site of action and possibly reducing the quantity of drug compound that is required in order to observe a clinically significant effect. Despite the fact that direct local application is preferred in medical practice, there can still be concerns regarding drug levels reached into the systemic circulation. For example, the treatment of airway diseases by local delivery by for instance inhalation, poses the risk of systemic exposure due to large amounts entering the GI tract and/or systemic absorption through the lungs. For the treatment of eye diseases by local delivery, also significant amounts of compound can enter the GI tract and/or systemic circulation due to the low permeability of the cornea, low capacity for fluid, efficient drainage and presence of blood vessels in the eyes and eyelids. Also for dermal applications, local injections and implantable medical devices, there is a severe risk of leakage into the systemic circulation. Therefore, in addition to the physical local application, it is preferable that the compounds display additional chemical or biological properties that will minimize systemic exposure.

Soft drugs are biologically active compounds that are inactivated once they enter the systemic circulation. This inactivation can be achieved in the liver, but the preferred inactivation should occur in the blood. These compounds, once applied locally to the target tissue/organ exert their desired effect locally. When they leak out of this target tissue/organ into the systemic circulation, they are very rapidly inactivated. Thus, soft drugs of choice are sufficiently stable in the target tissue/organ to exert the desired biological effect, but are rapidly degraded in the blood to biologically inactive compounds. In addition, it is highly preferable that the soft drugs of choice have retention at their biological target. This property will limit the number of daily applications and is highly desired to reduce the total load of drug and metabolites and in addition will significantly increase the patient compliance.

In conclusion, there is a continuing need to design and develop soft PDE4 inhibitors for the treatment of a wide range of disease states. The compounds described herein and pharmaceutically acceptable compositions thereof are useful for treating or lessening the severity of a variety of disorders or conditions that can be treated via modulation of PDE4 activity.

More specifically, the compounds of the invention are preferably used in the prevention and/or treatment of at least one disease or disorder, in which the PDE4 family is involved, such as several inflammatory diseases or fibrotic diseases, which can be treated via local application of a drug compound. Such diseases include, but are not limited to idiopathic pulmonary fibrosis, inflammatory eye diseases such as dry eye disease or allergic eye disease; inflammatory airway diseases such as asthma or chronic obstructive pulmonary disease, skin diseases such as atopic dermatitis or psoriasis and intestinal diseases such as inflammatory bowel disease.

SUMMARY OF THE INVENTION

We have surprisingly found that the compounds described herein act as inhibitors of PDE4. Compared to structurally related art-known PDE4 inhibitors, such as for example rolipram, roflumilast, piclamilast or the PDE4 inhibitors described in WO9520578 or EP0706795, the compounds of the present invention differ in that they are very rapidly converted into functionally inactive compounds for example by carboxylic ester hydrolases (EC 3.1.1) such as Cholinesterase or Paraoxonase 1 (PON1) or by plasma proteins displaying pseudoesterase activity such as Human serum albumin.

Carboxylic ester hydrolases (EC 3.1.1) represent a large group of enzymes involved in the degradation of carboxylic esters into alcohols and carboxylic acids. As such, enzymes displaying this catalytic activity are of potential interest for the design of soft kinase inhibitors. EC 3.1.1 includes the following sub-classes: EC 3.1.1.1 carboxylesterase, EC 3.1.1.2 arylesterase, EC 3.1.1.3 triacylglycerol lipase, EC 3.1.1.4 phospholipase A2, EC 3.1.1.5 lysophospholipase, EC 3.1.1.6 acetylesterase, EC 3.1.1.7 acetylcholinesterase, EC 3.1.1.8 cholinesterase, EC 3.1.1.10 tropinesterase, EC 3.1.1.11 pectinesterase, EC 3.1.1.13 sterol esterase, EC 3.1.1.14 chlorophyllase, EC 3.1.1.15 L-arabinonolactonase, EC 3.1.1.17 gluconolactonase, EC 3.1.1.19 uronolactonase, EC 3.1.1.20 tannase, EC 3.1.1.21 retinyl-palmitate esterase, EC 3.1.1.22 hydroxybutyrate-dimer hydrolase, EC 3.1.1.23 acylglycerol lipase, EC 3.1.1.24 3-oxoadipate enol-lactonase, EC 3.1.1.25 1,4-lactonase, EC 3.1.1.26 galactolipase, EC 3.1.1.27 4-pyridoxolactonase, EC 3.1.1.28 acylcarnitine hydrolase, EC 3.1.1.29 aminoacyl-tRNA hydrolase, EC 3.1.1.30 D-arabinonolactonase, EC 3.1.1.31 6-phosphogluconolactonase, EC 3.1.1.32 phospholipase A1, EC 3.1.1.33 6-acetylglucose deacetylase, EC 3.1.1.34 lipoprotein lipase, EC 3.1.1.35 dihydrocoumarin hydrolase, EC 3.1.1.36 limonin-D-ring-lactonase, EC 3.1.1.37 steroid-lactonase, EC 3.1.1.38 triacetate-lactonase, EC 3.1.1.39 actinomycin lactonase, EC 3.1.1.40 orsellinate-depside hydrolase, EC 3.1.1.41 cephalosporin-C deacetylase, EC 3.1.1.42 chlorogenate hydrolase, EC 3.1.1.43 α-amino-acid esterase, EC 3.1.1.44 4-methyloxaloacetate esterase, EC 3.1.1.45 carboxymethylenebutenolidase, EC 3.1.1.46 deoxylimonate A-ring-lactonase, EC 3.1.1.47 1-alkyl-2-acetylglycerophosphocholine esterase, EC 3.1.1.48 fusarinine-C ornithinesterase, EC 3.1.1.49 sinapine esterase, EC 3.1.1.50 wax-ester hydrolase, EC 3.1.1.51 phorbol-diester hydrolase, EC 3.1.1.52 phosphatidylinositol deacylase, EC 3.1.1.53 sialate O-acetylesterase, EC 3.1.1.54 acetoxybutynylbithiophene deacetylase, EC 3.1.1.55 acetylsalicylate deacetylase, EC 3.1.1.56 methylumbelliferyl-acetate deacetylase, EC 3.1.1.57 2-pyrone-4,6-dicarboxylate lactonase, EC 3.1.1.58 N-acetylgalactosaminoglycan deacetylase, EC 3.1.1.59 juvenile-hormone esterase, EC 3.1.1.60 bis(2-ethylhexyl)phthalate esterase, EC 3.1.1.61 protein-glutamate methylesterase, EC 3.1.1.63 11-cis-retinyl-palmitate hydrolase, EC 3.1.1.64 alltrans-retinyl-palmitate hydrolase, EC 3.1.1.65 L-rhamnono-1,4-lactonase, EC 3.1.1.66 5-(3,4-diacetoxybut-1-ynyl)-2,2'-bithiophene deacetylase, EC 3.1.1.67 fatty-acyl-ethyl-ester synthase, EC 3.1.1.68 xylono-1,4-lactonase, EC 3.1.1.70 cetraxate benzylesterase, EC 3.1.1.71 acetylalkylglycerol acetylhydrolase, EC 3.1.1.72 acetylxylan esterase, EC 3.1.1.73 feruloyl esterase, EC 3.1.1.74 cutinase, EC 3.1.1.75 poly(3-hydroxybutyrate) depolymerase, EC 3.1.1.76 poly(3-hydroxyoctanoate) depolymerase, EC 3.1.1.77 acyloxyacyl hydrolase, EC 3.1.1.78 polyneuridine-aldehyde esterase, EC 3.1.1.79 hormone-sensitive lipase, EC 3.1.1.80 acetylajmaline esterase, EC 3.1.1.81 quorum-quenching N-acyl-homoserine lactonase, EC 3.1.1.82 pheophorbidase, EC 3.1.1.83 monoterpene ε-lactone hydrolase, EC 3.1.1.84 cocaine esterase, EC 3.1.1.85 mannosylglycerate hydrolases.

An example of carboxylic ester hydrolase is Paraoxonase 1 (PON1). Paraxonase is also known as arylesterase (EC 3.1.1.2) or A-esterase. PON1 is a $Ca^{2+}$ dependent serum class A esterase, which is synthesized in the liver and secreted in the blood, where it associates exclusively with high-density lipoproteins (HDLs). Furthermore, it is able to cleave a unique subset of substrates including organophosphates, arylesters, lactones and cyclic carbonates. Therefore, the $R_2$ substituent of the compounds of the present invention, generally represented by formula I hereinbelow, can be selected to comprise a substituent selected from the group of arylesters, lactones and cyclic carbonates, more specifically from arylesters and lactones.

Cholinesterases represent additional examples of carboxylic ester hydrolases. Cholinesterases are enzymes that are primarily known for their role in the degradation of the neurotransmitter acetylcholine. Acetylcholinesterase (EC 3.1.1.7) is also known as Choline esterase I, true cholinesterase, RBC cholinesterase, erythrocyte cholinesterase, or acetylcholine acetylhydrolase. As suggested by some of its alternative names, acetylcholinesterase is not only found in brain, but also in the erythrocyte fraction of blood. In addition to its action on acetylcholine, acetylcholinesterase hydrolyzes a variety of acetic esters, and also catalyzes transacetylations. Acetylcholinesterase usually displays a preference for substrates with short acid chains, as the acetyl group of acetylcholine. Butyrylcholinesterase (EC 3.1.1.8) is also known as benzoylcholinesterase, choline esterase II, non-specific cholinesterase, pseudocholinesterase, plasma cholinesterase or acylcholine acylhydrolase, While being found primarily in liver, butyrylcholinesterase is also present in plasma. As indicated by some of its alternative names, it is less specific than acetylcholinesterase and will typically carry out the hydrolysis of substrates with larger acid chains (such as the butyryl group of butyrylcholine or the benzoyl group of benzolylcholine) at a faster rate than acetylcholinesterase. In addition to its action on acetylcholine, butyrylcholinesterase is known to participate in the metabolism of several ester drugs, such as procaine.

Human serum albumin (HSA) is a major component of blood plasma, accounting for approximately 60% of all plasma proteins. HSA has been found to catalyze the hydrolysis of various compounds such as aspirin, cinnamoylimidazole, p-nitrophenyl acetate, organophosphate insecticides, fatty acid esters or nicotinic esters. HSA displays multiple nonspecific catalytic sites in addition to its primary reactive site. The catalytic efficiency of these sites is however low, and HSA has often been described not as a true esterase, but as a pseudoesterase, In spite of its low catalytic efficiency, HSA can still play a significant role in the metabolism of drug-like compounds, because of its high concentration in plasma.

Unless a context dictates otherwise, asterisks are used herein to indicate the point at which a mono- or bivalent radical depicted is connected to the structure to which it relates and of which the radical forms part.

Viewed from a first aspect, the invention provides a compound of Formula I or a stereoisomer, tautomer, racemic, metabolite, pro- or predrug, salt, hydrate, or solvate thereof,

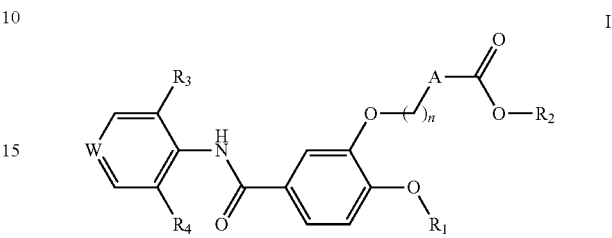

Wherein W is N, N=O, or $N^+$—$O^-$;
$R_1$ is selected from cycloalkyl or optionally substituted alkyl;
$R_2$ is an optionally substituted group selected from $C_{1-8}$alkyl, $C_{3-8}$cycloalkyl, heterocyclyl, aryl, and heteroaryl; or $R_2$ together with Y forms one of the following cyclic ester (lactone) structures

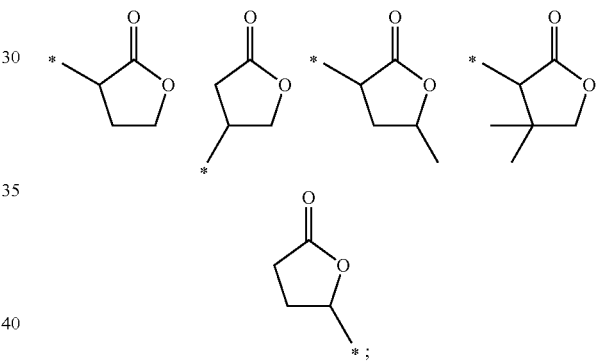

$R_3$ and $R_4$ are independently selected from hydrogen, $C_{1-8}$alkyl, or halo;
n is an integer from 0 to 9;
A is selected from the group consisting of a direct bond, —Z—Y, —C(=O)—NH—$R_{21}$, —C(=O)—NH—$R_{21}$—Z—Y—, —N($R_{22}$)—$R_{23}$—, and —Z-Cy-$(CH_2)_m$—: wherein
    Z is selected from a direct bond, O, NH, and S;
    $R_{21}$ is a direct bond or an optionally substituted $C_{1-8}$alkylene;
    $R_{22}$ is selected from hydrogen and $C_{1-8}$ alkyl;
    $R_{23}$ is an optionally substituted $C_{1-8}$alkylene;
    Cy is an optionally substituted cyclic structure selected from cycloalkyl, heterocyclyl, aryl, or heteroaryl; and
    m is selected from 0 and 1;
with the proviso that when Cy is dihydroisoxazole and m is 0, then $R_2$ is not methyl.

Viewed from a further aspect, the invention provides the use of a compound of the invention, or a composition comprising such a compound, for inhibiting the activity of at least one PDE4 isoform, in vitro or in vivo.

Viewed from a further aspect, the invention provides the use of a compound of the invention, or a composition comprising such a compound, for the treatment and/or prevention of a disease or condition associated with PDE4 activity and/or a disease or condition that may be alleviated by treatment with a PDE4 inhibitor. In particular, such use comprises administering to the patient a therapeutically effective amount of a compound of the present invention as described above.

Viewed from a further aspect, the invention provides a pharmaceutical and/or veterinary composition comprising a compound of the invention.

Viewed from a still further aspect, the invention provides a compound of the invention for use in human or veterinary medicine.

Viewed from a still further aspect, the invention provides the use of a compound of the invention in the preparation of a medicament for the prevention and/or treatment of immunological disorders, fibrotic diseases, or inflammatory diseases which can be treated via local application of a drug compound. Such diseases and disorders include, but are not limited to, idiopathic pulmonary fibrosis, inflammatory eye diseases such as dry eye disease or allergic eye disease; inflammatory airway diseases such as asthma or chronic obstructive pulmonary disease, skin diseases such as atopic dermatitis or psoriasis and intestinal diseases such as inflammatory bowel disease.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

Undefined (racemic) asymmetric centers that may be present in the compounds of the present invention are interchangeably indicated by drawing a wavy bonds or a straight bond in order to visualize the undefined steric character of the bond.

As already mentioned hereinbefore, in a first aspect the present invention provides compounds of Formula I

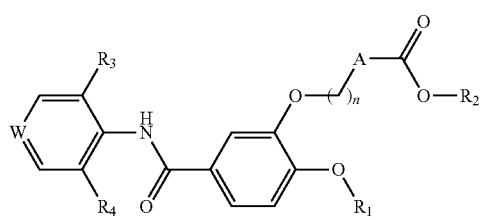

I

Wherein W, $R_1$, $R_2$, $R_3$, $R_4$ and n are as defined hereinbefore, including the stereoisomeric forms, solvates, and pharmaceutically acceptable addition salts thereof.

When describing the compounds of the invention, the terms used are to be construed in accordance with the following definitions, unless a context dictates otherwise: The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, carbonyl, nitro, amino, oxime, imino, azido, hydrazino, cyano, aryl, heteroaryl, cycloalkyl, heterocyclyl, acyl, alkylamino, alkoxy, thiol, alkylthio, carboxylic acid, acylamino, alkyl esters, carbamate, thioamido, urea, sulfonamido and the like. In a particular embodiment, such substituents are selected from the group consisting of halo, hydroxyl, nitro, amino, cyano, aryl (in particular phenyl and halophenyl such as fluorophenyl), heteroaryl (more in particular pyridinyl), cycloalkyl, heterocyclyl, alkoxy, alkylamino, and dialkylamino.

The term "alkylamino", as used herein refers to an amino group substituted with one or more alkyl chain(s). This definition includes quaternary ammonium derivatives.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, propynyl, butynyl, isobutynyl, pentynyl, hexynyl, and the like. An optionally substituted alkynyl refers to an alkynyl having optionally one or more substituents (for example 1, 2, 3 or 4), selected from those defined above for substituted alkyl.

The term "cycloalkyl" by itself or as part of another substituent is a cyclic alkyl group, that is to say, a monovalent, saturated, or unsaturated hydrocarbyl group having 1, 2, or 3 cyclic structure. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred. An "optionally substituted cycloalkyl" refers to a cycloalkyl having optionally one or more substituents (for example 1 to 3 substituents, for example 1, 2, 3 or 4 substituents), selected from those defined above for substituted alkyl. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a $C_3$ alkylene group may be for example *—$CH_2CH_2$ $CH_2$—*, *—CH(—$CH_2CH_3$)—*, or *—$CH_2$CH(— $CH_3$)—*. Likewise a $C_3$ cycloalkylene group may be

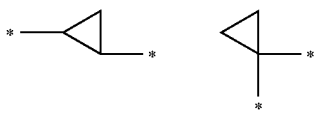

Where a cycloalkylene group is present, this is preferably a $C_3$-$C_6$ cycloalkylene group, more preferably a $C_3$ cycloalkylene (i.e. cyclopropylene group) wherein its connectivity to the structure of which it forms part is through a common carbon atom. Cycloalkylene and alkylene biradicals in compounds of the invention may be, but preferably are not, substituted.

The terms "heterocyclyl" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclic refers to a heterocyclic having optionally one or more substituents (for example 1 to 4 substituents, or for example 1, 2, 3 or 4), selected from those defined for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1,2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —$SO_2$—$NH_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —$SO_2R^a$, alkylthio, carboxyl, and the like, wherein $R^a$ is alkyl or cycloalkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno [3,2-b]furanyl, thieno[3,2-b]thiophenyl, thieno[2,3-d][1,3] thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1 (2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl; oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl),as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazoi-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno [3,2-b]furan-5-yl. The term "thieno[3,2-b]thiophenyl" as used herein includes thieno[3,2-b]thien-2-yl, thieno[3,2-b] thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3] thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo [1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl, indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo [b]thiophenyl, 6-benzo[b]thiophenyl and -7-benzo[b] thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl. The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, burin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quiriazolin-4-yl, quinazolin-5-yl, quinazolin-6-yl, quinazolin-7-yl and quinazolin-8-yl. The term "quinoxalinyl". as used herein includes quinoxalin-2-yl, quinoxalin-5-yl, and quinoxalin-6-yl. The term "7-azaindolyl" as used herein refers to 1H-Pyrrolo[2,3-b]pyridinyl and includes 7-azaindol-1-yl, 7-azaindol-2-yl, 7-azaindol-3-yl, 7-azaindol-4-yl, 7-azaindol-5-yl, 7-azaindol-6-yl. The term "6-azaindolyl" as used herein refers to 1H-Pyrrolo[2,3-c]pyridinyl and includes 6-azaindol-1-yl, 6-azaindol-2-yl, 6-azaindol-3-yl, 6-azaindol-4-yl, 6-azaindol-5-yl, 6-azaindol-7-yl. The term "5-azaindolyl" as used herein refers to 1H-Pyrrolo[3,2-c]pyridinyl and includes 5-azaindol-1-yl, 5-azaindol-2-yl, 5-azaindol-3-yl, 5-azaindol-4-yl, 5-azaindol-6-yl, 5-azaindol-7-yl. The term "4-azaindolyl" as used herein refers to 1H-Pyrrolo[3,2-b]pyridinyl and includes 4-azaindol-1-yl, 4-azaindol-2-yl, 4-azaindol-3-yl, 4-azaindol-5-yl, 4-azaindol-6-yl, 4-azaindol-7-yl.

For example, non-limiting examples of heteroaryl can be 2- or 3-furyl, 2- or 3-thienyl, 1-, 2- or 3-pyrrolyl, 1-, 2-, 4- or 5-imidazolyl, 1-, 3-, 4- or 5-pyrazolyl, 3-, 4- or 5-isoxazolyl, 2-, 4- or 5-oxazolyl, 3-, 4- or 5-isothiazolyl, 2-, 4- or 5-thiazolyl, 1,2,3-triazol-1-, -4- or -5-yl, 1,2,4-triazol-1-, -3-, -4- or -5-yl, 1H-tetrazol-1-, or -5-yl, 2H-tetrazol-2-, or -5-yl, 1,2,3-oxadiazol-4- or -5-yl, 1,2,4-oxadiazol-3- or -5-yl, 1,2,5-oxadiazolyl, 1,3,4-oxadiazolyl, 1,2,3-thiadiazol-4- or -5-yl, 1,2,4-thiadiazol-3- or -5-yl, 1,2,5-thiadiazol-3- or -4-yl, 1,3,4-thiadiazolyl, 1- or 5-tetrazolyl, 2-, 3- or 4-pyridyl, 3- or 4-pyridazinyl, 2-, 4-, 5- or 6-pyrimidyl, 2-, 3-, 4-, 5-6-2H-thiopyranyl, 2-, 3- or 4-4H-thiopyranyl, 4-azaindol-1-, 2-, 3-, 5-, or 7-yl, 5-azaindol-1-, or 2-, 3-, 4-, 6-, or 7-yl, 6-azaindol-1,2-, 3-, 4-, 5-, or 7-yl, 7-azaindol-1-, 2-, 3-, 4,5-, or 6-yl, 2-, 3-, 4-, 5-, 6- or 7-benzofuryl, 1-, 3-, 4- or 5-isobenzofuryl, 2-, 3-, 4-, 5-, 6- or 7-benzothienyl, 1-, 3-, 4- or 5-isobenzothienyl, 1-, 2-, 3-, 4-, 5-, 6- or 7-indolyl, 2- or 3-pyrazinyl, 1,4-oxazin-2- or -3-yl, 1,4-dioxin-2- or -3-yl, 1,4-thiazin-2- or -3-yl, 1,2,3-triazinyl, 1,2,4-triazinyl, 1,3,5-triazin-2-, -4- or -6-yl, thieno[2,3-b]furan-2-, -3-, -4-, or -5-yl, benzimidazol-1-yl, -2-yl, -4-yl, -5-yl, -6-yl, or -7-yl, 1-, 3-, 4-, 5-, 6- or 7-benzopyrazolyl, 3-, 4-, 5-, 6- or 7-benzisoxazolyl, 2-, 4-, 5-, 6- or 7-benzoxazolyl, 3-, 4-, 5-, 6- or 7-benzisothiazolyl, 1,3-benzothiazol-2-yl, -4-yl, -5-yl, -6-yl or -7-yl, 1,3-benzodioxol-4-yl, -5-yl, -6-yl, or -7-yl, benzotriazol-1-yl, -4-yl, -5-yl, -6-yl or -7-yl1-, 2-thianthrenyl, 3-, 4- or 5-isobenzofuranyl, 1-, 2-, 3-, 4- or 9-xanthenyl, 1-, 2-, 3- or 4-phenoxathiinyl, 2-, 3-pyrazinyl, 1-, 2-, 3-, 4-, 5-, 6-, 7- or 8-indolizinyl, 2-, 3-, 4- or 5-isoindolyl, 1H-indazol-1-yl, 3-yl, -4-yl, -5-yl, -6-yl, or -7-yl, 2H-indazol-2-yl, 3-yl, -4-yl, -5-yl, -6-yl, or -7-yl, imidazo[2,1-b][1,3]thiazoi-2-yl, imidazo[2,1-b][1,3]thiazol-3-yl, imidazo[2,1-b][1,3]thiazol-5-yl or imidazo[2,1-b][1,3]thiazol-6-yl, imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl or imidazo[1,2-a]pyridin-7-yl, tetrazolo[1,5-a]pyridine-5-yl, tetrazolo[1,5-a]pyridine-6-yl, tetrazolo[1,5-a]pyridine-7-yl, or tetrazolo[1,5-a]pyridine-8-yl, 2-, 6-, 7- or 8-purinyl, 4-, 5- or 6-phthalazinyl, 2-, 3- or 4-naphthyridinyl, 2-, 5- or 6-quinoxalinyl, 2-, 4-, 5-, 6-, 7- or 8-quinazolinyl, 1-, 2-, 3- or 4-quinolizinyl, 2-, 3-, 4-, 5-, 6-, 7-, or 8-quinolinyl(quinolyl), 2-, 4-, 5-, 6-, 7- or 8-quinazolyl, 1-, 3-, 4-, 5-, 6-, 7- or 8-isoquinolinyl(isoquinolyl), 3-, 4-, 5-, 6-, 7- or 8-cinnolinyl, 2-, 4-, 6- or 7-pteridinyl, 1-, 2-, 3-, 4- or 9-carbazolyl, 1-, 2-, 3-, 4-, 5-, 6-, 7-, 8- or 9-carbolinyl, 1-, 2-, 3-, 4-, 5-, 6-, 7-, 8-, 9- or 10-phenanthridinyl, 1-, 2-, 3- or 4-acridinyl, 1-, 2-, 3-, 4-, 5-, 6-, 7-, 8- or 9-perimidinyl, 2-, 3-, 4-, 5-, 6-, 7-, 8-, 9- or 10-(1,7)phenanthrolinyl, 1- or 2-phenazinyl, 1-, 2-, 3-, 4-, or 10-phenothiazinyl, 3- or 4-furazanyl, 1-, 2-, 3-, 4-, or 10-phenoxazinyl, or additionally substituted derivatives thereof.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "alkoxy" or "alkyloxy" as used herein refers to a radical having the Formula —OR$^b$ wherein R$^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "cycloalkylalkyl" by itself or as part of another substituent refers to a group having one of the aforementioned cycloalkyl groups attached to one of the aforementioned alkyl chains. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "heterocyclylalkyl" by itself or as part of another substituents refers to a group having one of the aforementioned heterocyclyl group attached to one of the aforementioned alkyl group, i.e., to a group —$R^d$—R' wherein $R^d$ is alkylene or alkylene substituted by alkyl group and $R^c$ is a heterocyclyl group.

The term "carboxy" or "carboxyl" or "hydroxycarbonyl" by itself or as part of another substituent refers to the group —$CO_2H$. Thus, a carboxyalkyl is an alkyl group as defined above having at least one substituent that is —$CO_2H$.

The term "alkoxycarbonyl" by itself or as part of another substituent refers to a carboxy group linked to an alkyl radical i.e. to form —C(=O)$OR^e$, wherein $R^e$ is as defined above for alkyl.

The term "alkylcarbonyloxy" by itself or as part of another substituent refers to a —O—C(=O)$R^e$ wherein $R^e$ is as defined above for alkyl.

The term "alkylcarbonylamino" by itself or as part of another substituent refers to an group of Formula —NH(C=O)R or —NR'(C=O)R, wherein R and R' are each independently alkyl or substituted alkyl.

The term "thiocarbonyl" by itself or as part of another substituent refers to the group —C(=S)—.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "haloaryl" alone or in combination, refers to an aryl radical having the meaning as defined above wherein one or more hydrogens are replaced with a halogen as defined above.

The term "haloalkoxy" alone or in combination refers to a group of Formula —O-alkyl wherein the alkyl group is substituted by 1, 2, or 3 halogen atoms. For example, "haloalkoxy" includes —$OCF_3$, —$OCHF_2$, —$OCH_2F$, —O—$CF_2$—$CF_3$, —O—$CH_2$—$CF_3$, —O—$CH_2$—$CHF_2$, and —O—$CH_2$—$CH_2F$.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

Where groups may be optionally substituted, such groups may be substituted once or more, and preferably once, twice or thrice. Substituents may be selected from, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to the compounds as depicted in examples, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those skilled in the art.

In a further embodiment, the present invention provides compounds of formula I

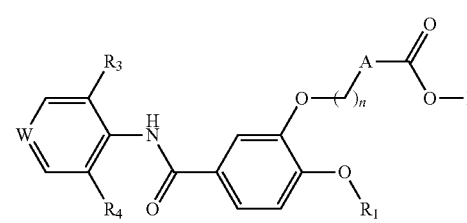

Wherein W is N, N=O, or $N^+$—$O^-$; in particular W is N;

$R_1$ is selected from cycloalkyl or optionally substituted alkyl; in particular optionally substituted alkyl; more in particular haloalkyl;

$R_2$ is an optionally substituted group selected from $C_{1-8}$alkyl, $C_{3-8}$cycloalkyl, heterocyclyl, aryl, and heteroaryl; or $R_2$ together with Y forms one of the following cyclic ester (lactone) structures

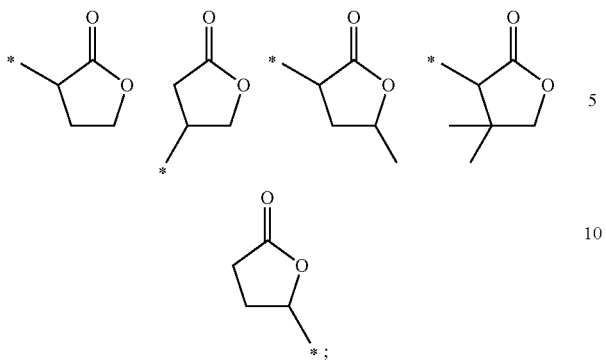

$R_3$ and $R_4$ are independently selected from hydrogen, $C_{1-8}$alkyl, or halo; in particular $R_3$ and $R_4$ are halo; more in particular chloro;

n is an integer from 0 to 9; in particular from 0 to 5;

A is selected from the group consisting of a direct bond, —Z—Y, —C(=O)—NH—$R_{21}$, —C(=O)—NH—$R_{21}$—Z—Y—, —N($R_{22}$)—$R_{23}$—, and —Z-Cy-(CH$_2$)$_m$—; in particular A is selected from the group consisting of a direct bond, —C(=O)—NH—$R_{21}$—Z—Y—, —N($R_{22}$)—$R_{23}$—, and —Z-Cy-(CH$_2$)$_m$— wherein Z is selected from a direct bond, O, NH, and S; in particular from a direct bond, NH and S;

$R_{21}$ is a direct bond or an optionally substituted $C_{1-8}$alkylene; in particular an optionally substituted $C_{1-8}$alkylene; more in particular $C_{1-8}$alkylene;

$R_{22}$ is selected from hydrogen and $C_{1-8}$ alkyl; in particular hydrogen;

$R_{23}$ is an optionally substituted $C_{1-8}$alkylene; in particular a $C_{1-8}$alkylene;

Cy is an optionally substituted cyclic structure selected from cycloalkyl, heterocyclyl, aryl, or heteroaryl; in particular an optionally substituted aryl; more in particular aryl; and m is selected from 0 and 1;

with the proviso that when Cy is dihydroisoxazole and m is 0, then $R_2$ is not methyl.

In another embodiment, the present invention provides compounds of formula I as defined hereinbefore, wherein $R_2$ is an selected from $C_{1-8}$alkyl, $C_{3-8}$cycloalkyl, heterocyclyl, aryl, and heteroaryl; wherein said $C_{1-8}$alkyl, $C_{3-8}$cycloalkyl, heterocyclyl, aryl, and heteroaryl is optionally substituted with halo, hydroxyl, nitro, amino, cyano, alkyl, alkenyl, alkynyl, alkoxy, —S-alkyl, alkylamino, dialkylamino, aryl, heteroaryl, cycloalkyl, and heterocyclyl; in particular $R_2$ is $C_{1-8}$alkyl or aryl; wherein said $C_{1-8}$alkyl and aryl are optionally substituted with halo, hydroxyl, nitro, amino, cyano, alkyl, alkenyl, alkynyl, alkoxy, —S-alkyl, alkylamino, dialkylamino, aryl, heteroaryl, cycloalkyl, and heterocyclyl; or $R_2$ together with Y forms one of the following cyclic ester (lactone) structures

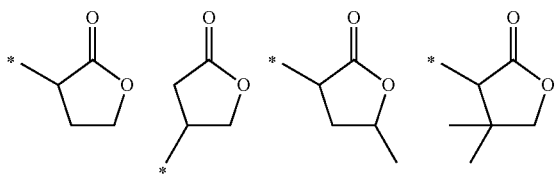

-continued

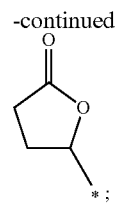

in particular

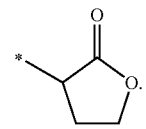

In a further embodiment, the present invention provides compounds of formula I as defined hereinbefore, wherein $R_2$ is $C_{1-8}$alkyl or aryl; wherein
said $C_{1-8}$alkyl is optionally substituted with a substituent selected from the group consisting of aryl, heterocyclyl, alkoxy, dialkylamino, and hydroxyl; and
said aryl is optionally substituted with halo; in particular fluoro; or $R_2$ together with Y forms one of the following cyclic ester (lactone) structures

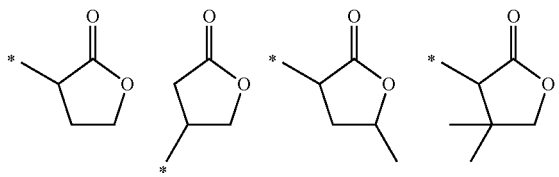

in particular

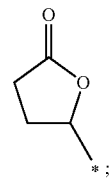

It is also an objective of the present invention to provide those compounds of formula I, wherein one or more of the following restrictions apply:

W is N;

$R_1$ is optionally substituted alkyl; in particular haloalkyl;

$R_1$ is $C_{1-6}$alkyl substituted with one or more halo groups; in particular methyl substituted with one or more halo groups; more in particular difluoromethyl;

$R_2$ is an optionally substituted group selected from $C_{1-8}$alkyl, $C_{3-8}$cycloalkyl, heterocyclyl, aryl, and heteroaryl; or $R_2$ together with Y forms one of the following cyclic ester (lactone) structures

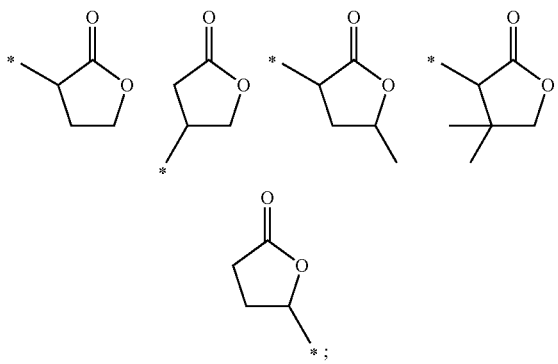

$R_2$ is an selected from $C_{1-8}$alkyl, $C_{3-8}$cycloalkyl, heterocyclyl, aryl, and heteroaryl; wherein said $C_{1-8}$alkyl, $C_{3-8}$cycloalkyl, heterocyclyl, aryl, and heteroaryl is optionally substituted with halo, hydroxyl, nitro, amino, cyano, alkyl, alkenyl, alkynyl, alkoxy, —S-alkyl, alkylamino, dialkylamino, aryl, heteroaryl, cycloalkyl, and heterocyclyl; in particular $R_2$ is $C_{1-8}$alkyl or aryl; wherein said $C_{1-8}$alkyl and aryl are optionally substituted with halo, hydroxyl, nitro, amino, cyano, alkyl, alkenyl, alkynyl, alkoxy, —S-alkyl, alkylamino, dialkylamino, aryl, heteroaryl, cycloalkyl, and heterocyclyl;

$R_2$ is $C_{1-8}$alkyl or aryl; wherein a) said $C_{1-8}$alkyl is optionally substituted with a substituent selected from the group consisting of aryl, heterocyclyl, alkoxy, dialkylamino, and hydroxyl; and b) said aryl is optionally substituted with halo; in particular fluoro;

$R_2$ together with Y may form one of the following cyclic ester (lactone) structures

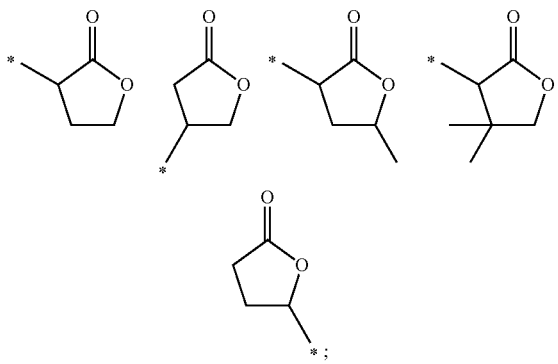

in particular

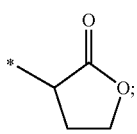

$R_3$ and $R_4$ are halo; in particular chloro;
n is an integer from 0 to 9; in particular from 0 to 5; more in particular from 0 to 4;
A is selected from the group consisting of a direct bond, —Z—Y, —C(=O)—NH—$R_{21}$—Z—Y—, —N($R_{22}$)—$R_{23}$—, and —Z-Cy-$(CH_2)_m$—;
Z is selected from a direct bond, NH, and S;
$R_{21}$ is $C_{1-8}$alkylene;
$R_{22}$ is hydrogen;
$R_{23}$ is $C_{1-8}$alkylene;
Cy is aryl;
m is selected from 0 and 1;
if Cy is dihydroisoxazole and m is 0, then $R_2$ is not methyl;
if Cy is a hydrogenated dihydroisoxazole and m is 0, then $R_2$ is not methyl;
if Cy is dihydroisoxazole, then $R_2$ is not methyl;
if Cy is isoxazole, isothiazole, a hydrogenated isoxazole, or a hydrogenated isothiazole, then $R_2$ is not methyl;
Cy can not be selected from hydrogenated isoxazole;
Cy can not be selected from isoxazole, isothiazole, a hydrogenated isoxazole, or a hydrogenated isothiazole.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

Viewed from a further aspect, the invention provides a compound of the invention for use as a medicine, in particular a human or veterinary medicine.

Viewed from a still further aspect, the invention provides a pharmaceutical composition comprising a compound of the invention.

In a preferred embodiment, the compounds of the present invention are useful as Phosphodiesterase inhibitors, more in particular for the inhibition of at least one PDE4 isoform, in particular as soft PDE4 inhibitors.

The present invention provides a compound of the invention, or a composition comprising such a compound for use in the prevention and/or treatment of a disease or a disorder associated with PDE4 activity or a disease or disorder that can be alleviated via treatment with a PDE4 inhibitor.

In a preferred embodiment, the present invention provides a compound of the invention for use in the prevention and/or treatment of at least one disease or disorder, which can be treated via local application of a drug compound, selected from the group comprising immunological disorders, fibrotic diseases, and inflammatory diseases. Such diseases and disorders include, but are not limited to, idiopathic pulmonary fibrosis, inflammatory eye diseases such as dry eye disease or allergic eye disease; inflammatory airway diseases such as asthma or chronic obstructive pulmonary disease, skin diseases such as atopic dermatitis or psoriasis and intestinal diseases such as inflammatory bowel disease.

In a further embodiment, the present invention provides the use of a compound of the invention, or a composition comprising such a compound in the prevention and/or treatment of a disease or a disorder associated with PDE4 activity or a disease or disorder that can be alleviated via treatment with a PDE4 inhibitor.

In a preferred embodiment, the present invention provides the use of a compound of the invention in the prevention and/or treatment of at least one disease or disorder, which can be treated via local application of a drug compound, selected from the group comprising immunological disorders, fibrotic diseases, and inflammatory diseases. Such diseases and disorders include, but are not limited to, idiopathic pulmonary fibrosis, inflammatory eye diseases such as dry eye disease or allergic eye disease; inflammatory airway diseases such as asthma or chronic obstructive pulmonary disease, skin diseases such as atopic dermatitis or psoriasis and intestinal diseases such as inflammatory bowel disease.

METHOD OF TREATMENT

The present invention further provides a method for the prevention and/or treatment of at least one disease, condition or disorder associated with the PDE4 activity (or diseases, conditions or disorders that can be alleviated by treatment with a PDE4 inhibitor); said method comprising administering to a subject in need thereof a therapeutically effective amount of a compound of the present invention, or a composition comprising such a compound.

In particular, the present invention provides a method for the prevention and/or treatment of at least one disease, condition or disorder associated with the PDE4 activity (or diseases, conditions or disorders that can be alleviated by treatment with a PDE4 inhibitor); said method comprising locally administering to a subject in need thereof a therapeutically effective amount of a compound of the present invention, or a composition comprising such a compound.

In a preferred embodiment, the present invention provides the use of a compound of the invention in the preparation of a medicament for the prevention and/or treatment of at least one disease or disorder which can be treated via local application of a drug compound comprising immunological disorders, fibrotic diseases, and inflammatory diseases including, but not limited to idiopathic pulmonary fibrosis, inflammatory eye diseases such as dry eye disease or allergic eye disease; inflammatory airway diseases such as asthma or chronic obstructive pulmonary disease, skin diseases such as atopic dermatitis or psoriasis, or intestinal diseases such as inflammatory bowel disease.

In the invention, particular preference is given to compounds of Formula I or any subgroup thereof that in the inhibition assay for PDE4 described below inhibit at least one PDE4 with an $IC_{50}$ value of less than 1 µM, preferably less than 100 nM.

Said inhibition may be effected in vitro and/or in vivo, and when effected in vivo, is preferably effected in a selective manner (versus other PDE families), as defined above.

The term "PDE4-mediated condition" or "disease", as used herein, means any disease or other deleterious condition in which PDE4 isoform(s) is (are) known to play a role. The term "PDE4-mediated condition" or "disease" also means those diseases or conditions that are alleviated by treatment with a PDE4 inhibitor. Accordingly, another embodiment of the present invention relates to treating or lessening the severity of one or more diseases in which phosphodiesterases, in particular PDE4 isoform(s), is (are) known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, benzoate, benzenesulfonate, bisulfate, citrate, camphorate, camphorsulfonate, fumarate, hemisulfate, hydrochloride, hydrobromide, hydroiodide, lactate, maleate, malonate, methanesulfonate, 2-naphthalene-sulfonate, oxalate, succinate, tartrate, and tosylate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

For the treatment of pain, the compounds of the invention may be used locally. For local administration, the compounds may advantageously be used in the form of a spray, ointment or transdermal patch or another suitable form for topical, transdermal and/or intradermal administration.

For ophthalmic application, solutions, gels, tablets and the like are often prepared using a physiological saline solution, gel or excipient as a major vehicle. Ophthalmic formulations should preferably be prepared at a comfortable pH with an appropriate buffer system.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intramuscular or intranasal routes, depending mainly on the specific preparation used and the condition to be treated or prevented. The at least one compound of the invention will generally be administered in an "effective amount", by which is meant any amount of a compound of the Formula I, II or III or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.001 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses, or essentially continuously. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

A. Physicochemical Properties of the Compounds

A.1. Compound Purity

Unless indicated otherwise, the purity of the compounds was confirmed by liquid chromatography/mass spectrometry (LC/MS)

A.2. Attribution of the Configuration

The Cahn-Ingold-Prelog system was used to attribute the absolute configuration of chiral center, in which the four groups on an asymmetric carbon are ranked to a set of sequences rules. Reference is made to Cahn; Ingold; Prelog *Angew. Chem. Int. Ed. Engl.* 1966, 5, 385-415.

A.3. Stereochemistry

It is known by those skilled in the art that specific enantiomers (or diastereoisomers) can be obtained by different methods such as, but not limited to chiral resolution (for example, salts formed with optically active acids or bases may be used to form diastereoisomeric salts that can facilitate the separation of optically active isomers of the compounds of Formula I or any subgroup thereof), assymetric synthesis or preparative chiral chromatography (using different column such as Chiralcel OD-H (tris-3,5-dimethylphenylcarbamate, 46×250 or 100×250 mm, 5 µm), Chiralcel OJ (tris-methylbenzoate, 46×250 or 100×250 mm, 5 µm), Chiralpak AD (tris-3,5-dimethylphenylcarbamate, 46×250 mm, 10 µm) and Chiralpak AS (tris-(S)-1-phenylethylcarbamate, 46×250 mm, 10 µm) from Chiral Technologies Europe (Illkirch, France)). Whenever it is convenient, stereoisomers can be obtained starting from commercial materials with known configuration (such compounds include aminoacid for instance).

B. Compound Synthesis

The compounds of the invention may be prepared by methods well known to those skilled in the art, and as described in the synthetic and experimental procedures shown below.

B.1. Intermediates

Intermediate 1

4-(difluoromethoxy)-3-hydroxybenzaldehyde

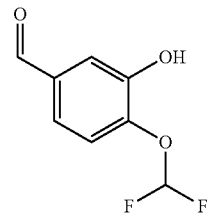 [SMILES: O=Cc1ccc(OC(F)F)c(O)c1]

To a solution of 3,4-dihydroxybenzaldehyde (41.52 g, 0.3 mol, 1.0 eq) and sodium chloro(difluoro)acetate (45.75 g, 0.3 mol, 1.0 eq) in DMF (375 ml) and water (7.5 ml) was added NaOH (12 g, 0.3 mol, 1.0 eq) and the resulting mixture was heated at 120° C. for 2 h. The solvent was removed by vacuum distillation and HCl and water were added to the residue. The mixture was extracted with EA (500 ml×2) and the solvent was removed under reduced pressure. The crude product was purified by chromatography on silica gel (PE/EA from 10/1 to 8/1) to furnish Intermediate 1 (20.86 g, 36.9% yield, 99.8% purity) as a white solid.

Intermediate 2 propyl 5-[2-(difluoromethoxy)-5-formylphenoxy]pentanoate

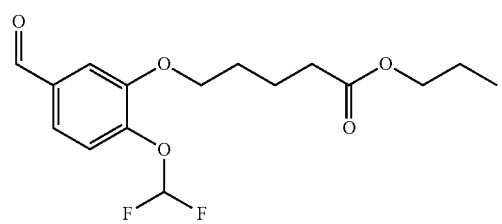 [SMILES: CCCOC(=O)CCCCOc1cc(C=O)ccc1OC(F)F]

A mixture of Intermediate 1 (3.7 g, 19.6 mmol, 1.0 eq), propyl 5-bromopentanoate (4.6 g, 20.6 mmol, 1.05 eq) and $K_2CO_3$ (5.4 g, 39.2 mmol, 2.0 eq) in $CH_3CN$ (50 ml) was refluxed under $N_2$ for 4 h. The yellow mixture was cooled to room temperature, diluted with water and extracted with EA. Evaporation of the solvent under reduced pressure afforded the crude product as yellow oil. Purification by chromatography (silica gel, PE/EA from 5/1 to 3/1) yielded Intermediate 2 (5.9 g, 60.8% yield, 99.7% purity) as colorless oil.

Intermediate 3

4-(difluoromethoxy)-3-[(5-oxo-5-propoxypentyl) oxy]benzoic acid

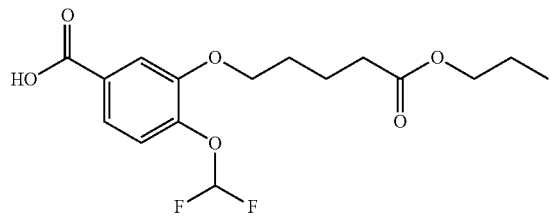 [SMILES: CCCOC(=O)CCCCOc1cc(C(=O)O)ccc1OC(F)F]

To a solution of Intermediate 2 (5.9 g, 17.9 mmol, 1.0 eq) in 80% AcOH (aq) (150 ml) was added $H_2NSO_3H$ (2.58 g, 26.8 mmol, 1.5 eq) at 10° C. A solution of $NaClO_2$ (2.47 g, 26.8 mmol, 1.5 eq) in water (10 ml) at 5~10° C. was added dropwise to this reaction mixture. After stirring at 10° C. for another 30 min, the mixture was diluted with water (200 ml) and extracted with EA (150 ml×2). Evaporation of the solvent under reduced pressure afforded Intermediate 3 (6.2 g, 100% yield, 93.33% purity) as an off-white solid.

Intermediate 4

5-[5-{[(3,5-dichloropyridin-4-yl)amino]carbonyl}-2-(difluoromethoxy) phenoxy]pentanoic acid

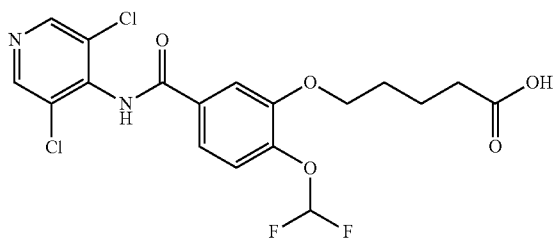 [SMILES: O=C(O)CCCCOc1cc(C(=O)Nc2c(Cl)cncc2Cl)ccc1OC(F)F]

3,5-Dichloropyridin-4-amine (3.8 g, 23.3 mmol, 1.3 eq) was added in portions to a suspension of 60% NaH (1.58 g, 39.4 mmol, 2.2 eq) in anhydrous THF (50 ml) at 5° C.

In a separate flask, a mixture of Intermediate 3 (6.2 g, 17.9 mmol, 1.0 eq) and $SOCl_2$ (6.39 g, 53.7 mmol, 3.0 eq) in toluene (100 ml) was heated at 90° C. for 1.5 h. The solvent was evaporated and the yellow oily residue was dissolved in anhydrous THF (50 ml). This solution was added dropwise to the prepared suspension of 3,5-dichloropyridin-4-amine and NaH in THF at 0-10° C. under $N_2$. After stirring at 10° C. for 1 h, the yellow mixture was acidified to pH=2 with 1N HCl. The resulting mixture was extracted with EA (150 ml×2) and the solvent was evaporated under reduced pressure. The solid residue was purified by chromatography (silica gel, PE/EA from 2/1 to 1/1) to afford Compound 1 (4.5 g, 51.1% yield, 96.45% purity) as an off-white solid.

A mixture of Compound 1 (2.0 g, 4.1 mmol, 1.0 eq) in MeOH (20 ml) and 20 ml of a 1M solution of LiOH (20 mmol, 5.0 eq) was heated at 60° C. for 80 min. The mixture was cooled to room temperature, acidified to pH=4 with 1N HCl and extracted with EA (80 ml×2). Evaporation of the solvent under reduced pressure afforded Intermediate 4 (1.8 g, 100% yield, 97.61% purity) as a white solid.

Intermediate 5

3-(4-bromobutoxy)-4-(difluoromethoxy)benzaldehyde

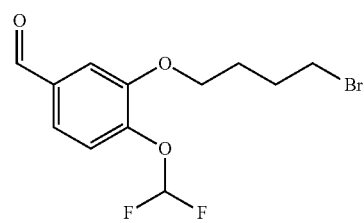 [SMILES: O=Cc1ccc(OC(F)F)c(OCCCCBr)c1]

A mixture of Intermediate 1 (7.7 g, 40.9 mmol, 1.0 eq), 1,4-dibromobutane (14.1 g, 65.5 mmol, 1.6 eq) and $K_2CO_3$ (11.2 g, 81 mmol, 2 eq) in $CH_3CN$ (100 ml) was refluxed under $N_2$ for 1.5 h. The white mixture was cooled to room temperature, filtered and the filtrate was evaporated under vacuum. The yellow oily residue was purified by chromatography (silica gel, PE/EA from 10/1 to 6/1) to afford Intermediate 5 (10.0 g, 75.8% yield) as a colorless oil.

Intermediate 6

3-(4-bromobutoxy)-4-(difluoromethoxy)benzoic acid

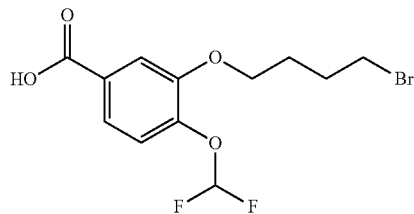 [SMILES: O=C(O)c1ccc(OC(F)F)c(OCCCCBr)c1]

To a solution of Intermediate 5 (10 g, 30.9 mmol, 1.0 eq) in 80% AcOH (200 ml) was added $H_2NSO_3H$ (4.5 g, 46.4 mmol, 1.5 eq) at 10° C. A solution of $NaClO_2$ (4.3 g, 46.4 mmol, 1.5 eq) in water (20 ml) was added dropwise to the resulting solution at 5-10° C. After stirring at 10° C. for another 30 min, the mixture was poured on ice-water (400 ml) and the product was collected by filtration and washed with EA (50 ml). Extraction with EA (400 ml) to remove water and evaporation of the organic fraction under vacuum afforded Intermediate 6 (10.2 g, 97.1% yield) as a white solid.

Intermediate 7

3-(4-bromobutoxy)-N-(3,5-dichloropyridin-4-yl)-4-(difluoromethoxy)benzamide

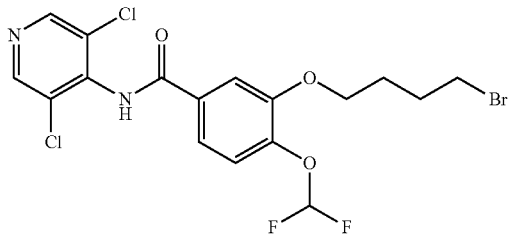 [SMILES: O=C(Nc1c(Cl)cncc1Cl)c1ccc(OC(F)F)c(OCCCCBr)c1]

To a suspension of 60% NaH (2.6 g, 65.6 mmol, 2.2 eq) in anhydrous THF (70 ml) was added 3,5-dichloropyridin-4-amine (5.3 g, 32.8 mmol, 1.3 eq) in portions at 5° C.

In a separate flask, a mixture of Intermediate 6 (10.1 g, 29.8 mmol, 1.0 eq) and SOCl$_2$ (11.7 g, 98.3 mmol, 3.0 eq) in toluene (150 ml) was heated at 90° C. for 1.5 h. The solvent was evaporated and the yellow oily residue was dissolved in anhydrous THF (80 ml). This solution was added dropwise to the prepared suspension of 3,5-dichloropyridin-4-amine and NaH in THF at 0-10° C. under N$_2$. After stirring at 10° C. for another 30 min, the yellow mixture was acidified to pH=2 with 1N HCl. The resulting mixture was extracted with EA (100 ml×3), and evaporated under reduced pressure to afford Intermediate 7 (14.4 g, 92.9% yield) as an off-white solid.

Intermediate 8

3-(4-aminobutoxy)-N-(3,5-dichloropyridin-4-yl)-4-(difluoromethoxy)benzamide

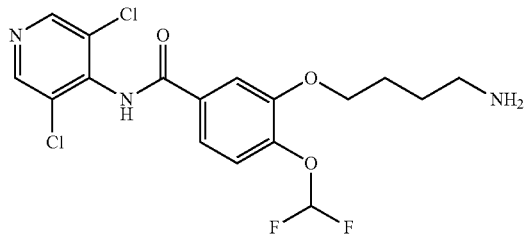 [SMILES: NCCCCOc1cc(C(=O)Nc2c(Cl)cncc2Cl)ccc1OC(F)F]

A mixture of Intermediate 7 (2 g, 4.1 mmol, 1.0 eq) and a 8% NH$_4$OH solution (160 ml) was refluxed for 3 h. The reaction mixture was filtered while hot, and the filtrate was cooled to 10° C. A solid was formed, collected by filtration and washed with water, MeOH and Et$_2$O. This afforded Intermediate 8 (800 mg, 46.0% yield) as an off-white solid.

Intermediate 9

3-(3-bromopropoxy)-4-(difluoromethoxy)benzaldehyde

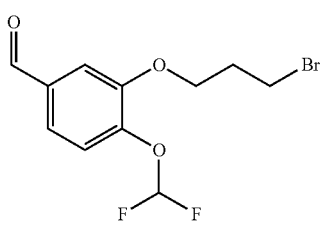 [SMILES: O=Cc1ccc(OC(F)F)c(OCCCBr)c1]

Intermediate 9 was obtained from Intermediate 1 (15.0 g, 80 mmol, 1.0 eq) and 1,3-dibromopropane (26.0 g, 160 mmol, 2.0 eq), using an experimental procedure analogous to the one used for obtaining Intermediate 5 (20.0 g, 81% yield).

Intermediate 10

3-(4-bromopropoxy)-4-(difluoromethoxy)benzoic acid

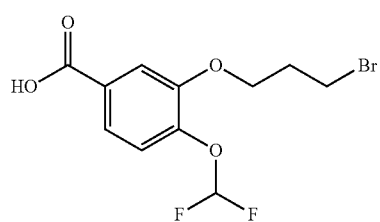 [SMILES: O=C(O)c1ccc(OC(F)F)c(OCCCBr)c1]

Intermediate 10 was obtained from Intermediate 9 (15.0 g, 48.5 mmol, 1.0 eq), using an experimental procedure analogous to the one used for obtaining Intermediate 6 (12.0 g, 76% yield).

Intermediate 11

3-(4-bromopropoxy)-N-(3,5-dichloropyridin-4-yl)-4-(difluoromethoxy)benzamide

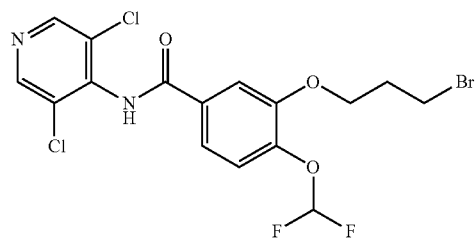 [SMILES: O=C(Nc1c(Cl)cncc1Cl)c1ccc(OC(F)F)c(OCCCBr)c1]

Intermediate 11 was obtained from Intermediate 10 (10.0 g, 30.8 mmol, 1.0 eq) and 3,5-dichloropyridin-4-amine (6.5 g, 40 mmol, 1.3 eq), using an experimental procedure analogous to the one used for obtaining Intermediate 7 (5.0 g, 34% yield).

Intermediate 12

2-[(3-{5-[(3,5-dichloropyridin-4-yl)carbamoyl]-2-(difluoromethoxy)phenoxy}propyl)amino]acetic acid

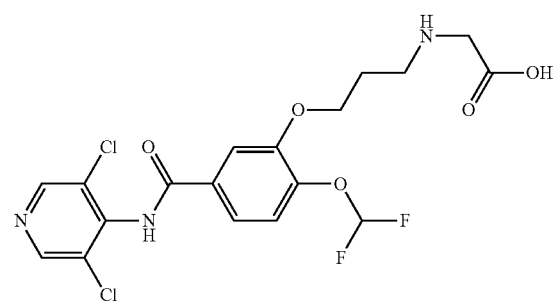 [SMILES: O=C(O)CNCCCOc1cc(C(=O)Nc2c(Cl)cncc2Cl)ccc1OC(F)F]

Intermediate 12 was obtained by hydrolysis of Compound 15 (602 mg, 1.26 mmol, 1.0 eq) by LiOH (201 mg, 5.04 mmol, 4.0 eq), using a procedure analogous to the final step used for obtaining Intermediate 4; the required changes in the experimental setup being straightforward to those skilled in the art (0.3 g, 51% yield).

Intermediate 13

3-[(3-{5-[(3,5-dichloropyridin-4-yl)carbamoyl]-2-(difluoromethoxy) phenoxy}propyl)sulfanyl]benzoic acid

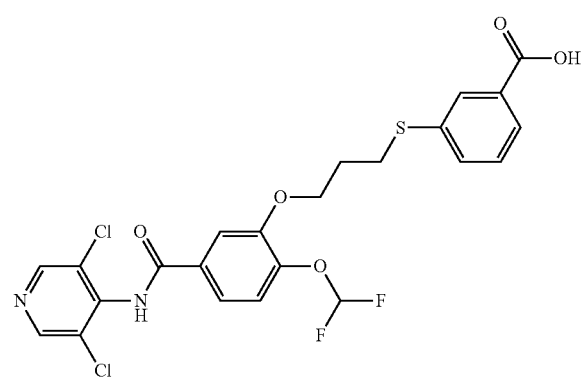 [SMILES: O=C(O)c1cccc(SCCCOc2cc(C(=O)Nc3c(Cl)cncc3Cl)ccc2OC(F)F)c1]

Intermediate 13 was obtained by hydrolysis of Compound 17 (300 mg, 0.53 mmol, 1.0 eq) by LiOH (84.4 mg, 2.12 mmol, 4.0 eq), using a procedure analogous to the final step used for obtaining Intermediate 4; the required changes in the experimental setup being straightforward to those skilled in the art (250 mg, 87% yield).

Intermediate 14

4-[(3-{5-[(3,5-dichloropyridin-4-yl)carbamoyl]-2-(difluoromethoxy) phenoxy}propyl)sulfanyl]benzoic acid

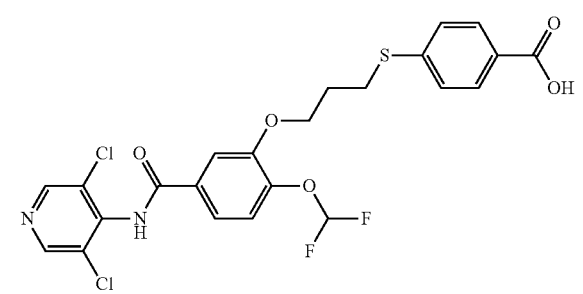 [SMILES: O=C(O)c1ccc(SCCCOc2cc(C(=O)Nc3c(Cl)cncc3Cl)ccc2OC(F)F)cc1]

Intermediate 14 was obtained by hydrolysis of Compound 18 (350 mg, 0.61 mmol, 1.0 eq) by LiOH (97.9 mg, 2.44 mmol, 4.0 eq), using a procedure analogous to the final step used for obtaining Intermediate 4; the required changes in the experimental setup being straightforward to those skilled in the art (270 mg, 87% yield).

Intermediate 15 methyl 4-(2-(difluoromethoxy)-5-formylphenoxy)benzoate

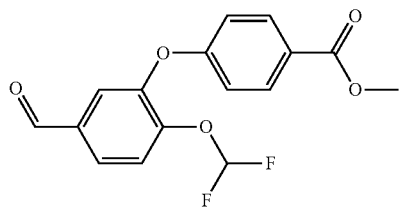 [SMILES: COC(=O)c1ccc(Oc2cc(C=O)ccc2OC(F)F)cc1]

A mixture of Intermediate 1 (0.44 g, 2.3 mmol, 1.0 eq), Cu(OAc)$_2$ (0.44 g, 2.3 mmol, 1.0 eq), pyridine (0.37 g, 4.6 mmol, 2.0 eq) and (4-(methoxycarbonyl)phenyl)boronic acid (0.8 g, 4.6 mmol, 2.0 eq) in anhydrous DCM (20 ml) was stirred at room temperature for 15 hrs. The mixture was filtered and the filtrate was extracted with DCM (20 ml×2). The combined organic fractions were dried and concentrated to give crude product, which was purified by column chromatography (silica gel, PE/EA from 1/0 to 3/1) to give Intermediate 15 (0.5 g, 67%) as a white solid.

Intermediate 16

4-(difluoromethoxy)-3-(4-(methoxycarbonyl)phenoxy)benzoic acid

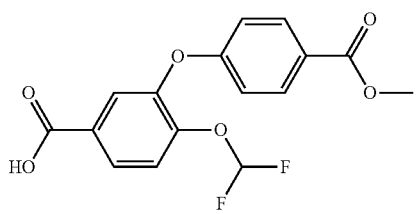 [SMILES: COC(=O)c1ccc(Oc2cc(C(=O)O)ccc2OC(F)F)cc1]

Intermediate 16 was obtained from Intermediate 15 (0.5 g, 1.55 mmol, 1.0 eq), using an experimental procedure analogous to the one used for obtaining Intermediate 6 (0.5 g, 95% yield).

Intermediate 17

4-{5-[(3,5-dichloropyridin-4-yl)carbamoyl]-2-(difluoromethoxy)phenoxy}benzoic acid

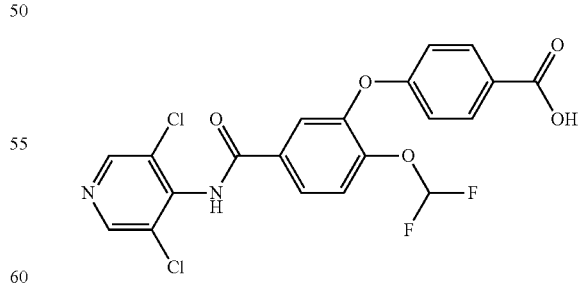

Intermediate 17 was obtained by hydrolysis of Compound 21 (0.5 g, 1.05 mmol, 1.0 eq) by LiOH (0.479 g, 20 mmol, 19.0 eq), using a procedure analogous to the final step used for obtaining intermediate 4; the required changes in the experimental setup being straightforward to those skilled in the art (0.37 g, 75% yield).

Intermediate 18 ethyl 3-(2-(difluoromethoxy)-5-formyl phenoxy)benzoate

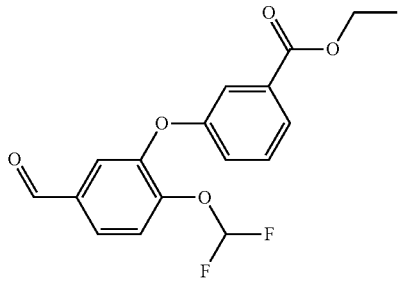 [SMILES: CCOC(=O)c1cccc(Oc2cc(C=O)ccc2OC(F)F)c1]

Intermediate 18 was obtained from Intermediate 1 (0.44 g, 2.3 mmol, 1.0 eq) and (3-(ethoxycarbonyl)phenyl)boronic acid (0.8 g, 4.5 mmol, 1.95 eq), using an experimental procedure analogous to the one used for obtaining Intermediate 15 (0.6 g, 78% yield).

Intermediate 19

4-(difluoromethoxy)-3-(3-(ethoxycarbonyl)phenoxy) benzoic acid

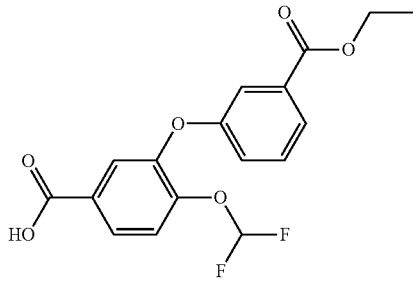 [SMILES: CCOC(=O)c1cccc(Oc2cc(C(=O)O)ccc2OC(F)F)c1]

Intermediate 19 was obtained from Intermediate 18 (0.6 g, 1.78 mmol, 1.0 eq), using an experimental procedure analogous to the one used for obtaining Intermediate 6 (0.6 g, 94% yield).

Intermediate 20

3-{5-[(3,5-dichloropyridin-4-yl)carbamoyl]-2-(difluoromethoxy)phenoxy}benzoic acid

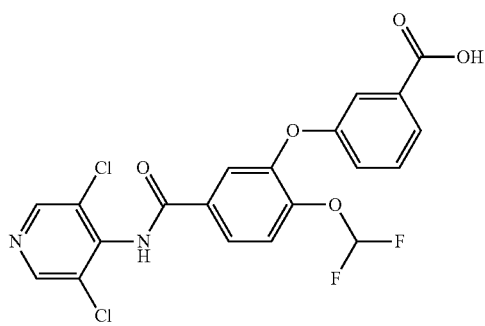 [SMILES: O=C(O)c1cccc(Oc2cc(C(=O)Nc3c(Cl)cncc3Cl)ccc2OC(F)F)c1]

Intermediate 20 was obtained by hydrolysis of Compound 22 (0.5 g, 1.0 mmol, 1.0 eq) by LiOH (0.479 g, 20 mmol, 20.0 eq), using a procedure analogous to the final step used for obtaining Intermediate 4; the required changes in the experimental setup being straightforward to those skilled in the art (0.41 g, 85% yield).

B.2. Compounds of the Invention

B.2.1 Compounds of the Invention: Pyridines

Compound 1 propyl 5-[5-{[(3,5-dichloropyridin-4-yl)amino]carbonyl}-2-(difluoromethoxy) phenoxy]pentanoate

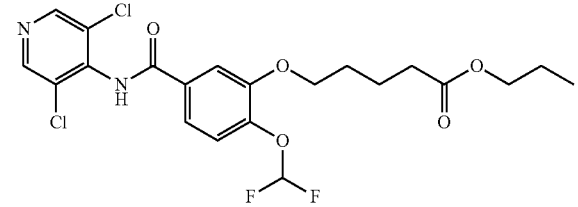 [SMILES: CCCOC(=O)CCCCOc1cc(C(=O)Nc2c(Cl)cncc2Cl)ccc1OC(F)F]

The synthesis of Compound 1 is described hereinabove as part of the synthesis of Intermediate 4.

Compound 2 phenyl 5-[5-{[(3,5-dichloropyridin-4-yl)amino]carbonyl}-2-(difluoromethoxy)phenoxy]pentanoate

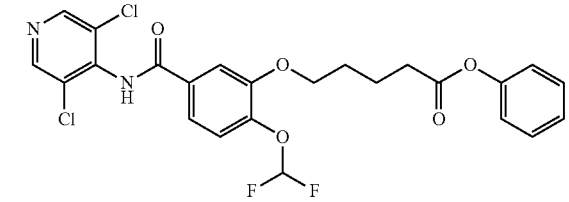 [SMILES: O=C(CCCCOc1cc(C(=O)Nc2c(Cl)cncc2Cl)ccc1OC(F)F)Oc1ccccc1]

A mixture of Intermediate 4 (225 mg, 0.5 mmol, 1.0 eq), PhOH (50 mg, 0.55 mmol, 1.1 eq), DCC (113 mg, 0.55 mmol, 1.1 eq) and DMAP (12 mg, 0.1 mmol, 0.2 eq) in DCM (20 ml) was stirred at 15° C. for 2.5 h under $N_2$. The mixture was filtered and the filtrate was concentrated under vacuum. The crude product was purified by chromatography (silica gel, PE/EA 2/1) and evaporated, a 2/1 mixture of PE/EA (45 ml) was added and the resulting suspension was filtered. The filtrate was concentrated under reduced pressure to afford Compound 2 (200 mg, 76.9% yield, 98.52% purity) as a white solid.

Compounds 3-10

The following compounds of the invention were obtained using a procedure analogous to the one used for the synthesis of Compound 2.

| Cpd | Structure | Intermediate | Reagent | Yield (%) |
|---|---|---|---|---|
| 3 | 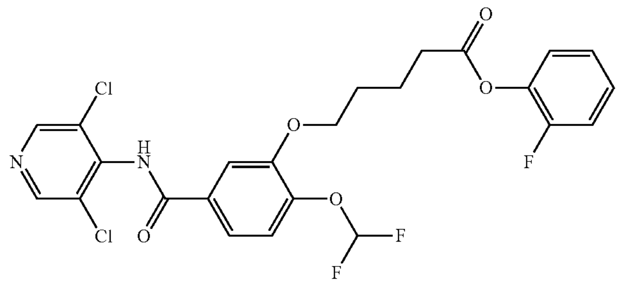 [SMILES: O=C(CCCCOc1cc(C(=O)Nc2c(Cl)cncc2Cl)ccc1OC(F)F)Oc1ccccc1F] | 4 | 2-fluorophenol | 55.3 |
| 4 | 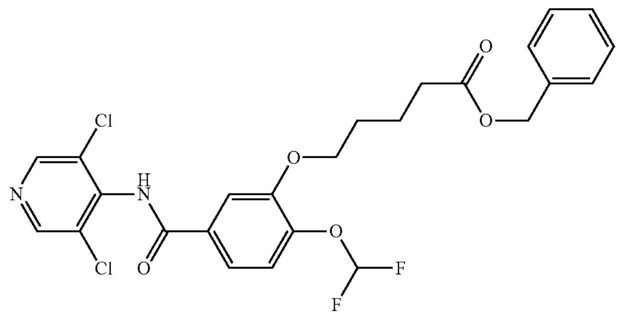 [SMILES: O=C(CCCCOc1cc(C(=O)Nc2c(Cl)cncc2Cl)ccc1OC(F)F)OCc1ccccc1] | 4 | benzyl alcohol | 32.0 |
| 5 | 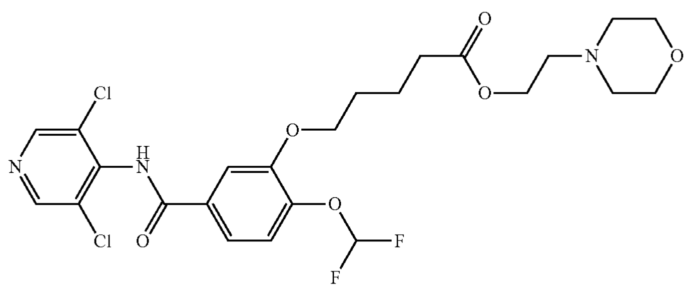 [SMILES: O=C(CCCCOc1cc(C(=O)Nc2c(Cl)cncc2Cl)ccc1OC(F)F)OCCN1CCOCC1] | 4 | 2-morpholinoethanol | 23.4 |
| 6 | 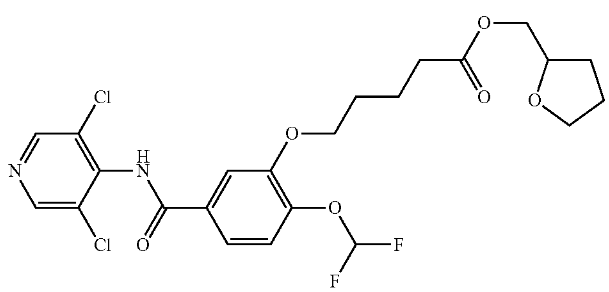 [SMILES: O=C(CCCCOc1cc(C(=O)Nc2c(Cl)cncc2Cl)ccc1OC(F)F)OCC1CCCO1] | 4 | tetrahydrofurfuryl alcohol | 25.4 |
| 7 | 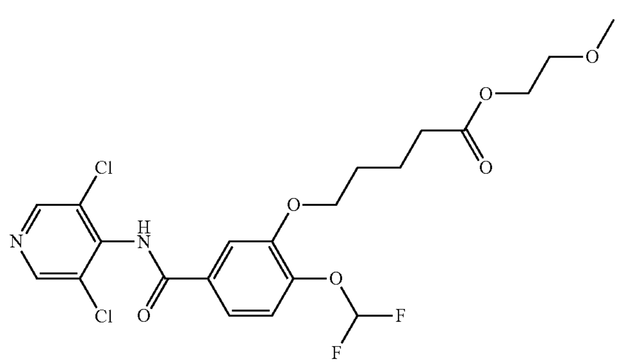 [SMILES: COCCOC(=O)CCCCOc1cc(C(=O)Nc2c(Cl)cncc2Cl)ccc1OC(F)F] | 4 | 2-methoxyethanol | 33.4 |

-continued

| Cpd | Structure | Intermediate | Reagent | Yield (%) |
|---|---|---|---|---|
| 8 | 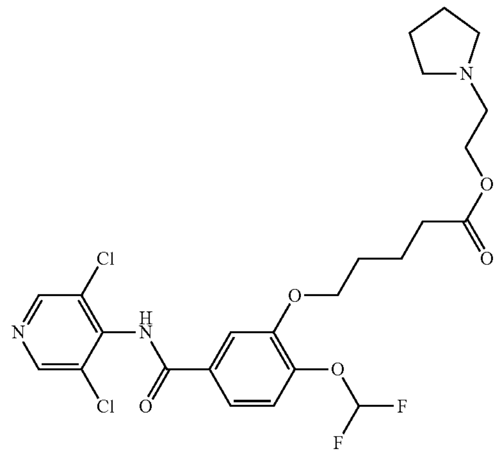 [SMILES: O=C(CCCCOc1cc(C(=O)Nc2c(Cl)cncc2Cl)ccc1OC(F)F)OCCN1CCCC1] | 4 | | 24.7 |
| 9 | 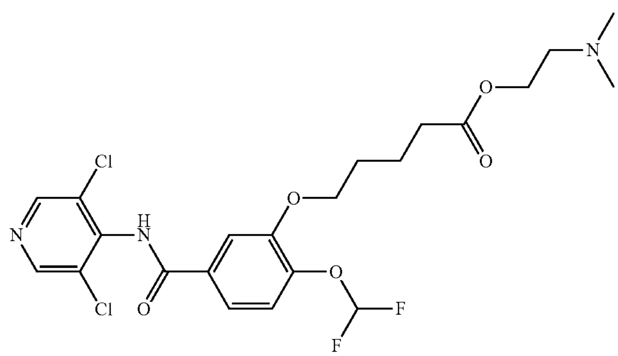 [SMILES: CN(C)CCOC(=O)CCCCOc1cc(C(=O)Nc2c(Cl)cncc2Cl)ccc1OC(F)F] | 4 | | 21.5 |
| 10 | 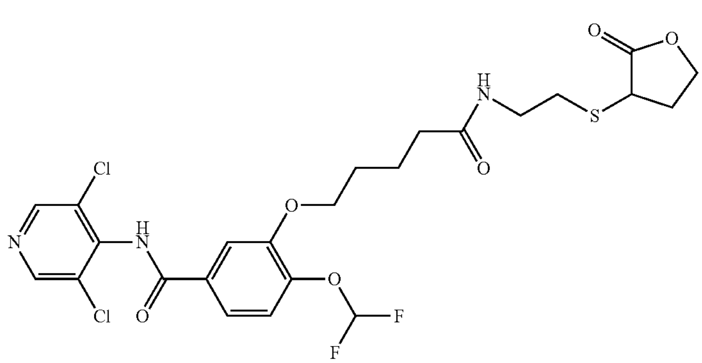 [SMILES: O=C(CCCCOc1cc(C(=O)Nc2c(Cl)cncc2Cl)ccc1OC(F)F)NCCSC1CCOC1=O] | 4 | | 24.8 |

Compound 11

N-(3,5-dichloropyridin-4-yl)-4-(difluoromethoxy)-3-{4-[(2-oxotetrahydro furan-3-yl)amino]butoxy}benzamide

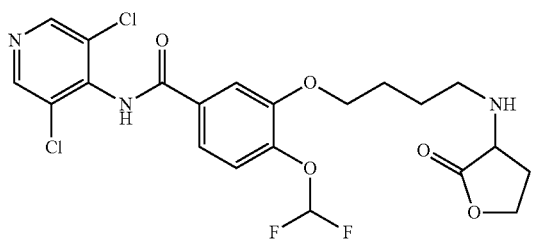 [SMILES: O=C(Nc1c(Cl)cncc1Cl)c1ccc(OC(F)F)c(OCCCCNC2CCOC2=O)c1]

A mixture of Intermediate 8 (1.0 g, 2.38 mmol, 1.0 eq), $K_2CO_3$ (0.70 g, 5.07 mmol, 2.0 eq) and 3-bromodihydrofuran-2(3H)-one (0.39 g, 2.38 mmol, 1.0 eq) in DMF (10 ml) was heated at 90° C. for 1 h. The reaction mixture was cooled to room temperature and water (30 ml) was added. After extraction with EA (40 ml×3) and evaporation of solvent, the residue was purified by chromatography (silica gel, EA) to give thick, light yellow oil. The crude product was dissolved in EA (3.5 ml), and subsequently ether (35 ml) and PE (14 ml) were added dropwise. The precipitate was filtered to afford Compound 11 (0.7 g, 58.3% yield, 96.66% purity).

Compound 12

N-(3,5-dichloropyridin-4-yl)-4-(difluoromethoxy)-3-{4-[(2-oxotetrahydro furan-3-yl)thio]butoxy}benzamide

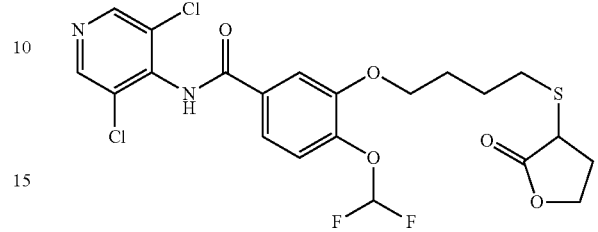

A mixture of Intermediate 7 (0.87 g, 1.8 mmol, 1.0 eq), 3-sulfanyldihydrofuran-2(3H)-one (0.21 g, 1.8 mmol, 1.0 eq), and $K_2CO_3$ (0.50 g, 3.6 mmol, 2.0 eq) in $CH_3CN$ (20 ml) was refluxed for 1.5 h. The reaction mixture was cooled to room temperature, filtered and the filtrate was evaporated under reduced pressure. The yellow semi-solid was dissolved in EA (5 ml) and purified by chromatography (silica gel, PE/EA from 1/1 to 1/2) to afford Compound 12 (0.80 g, 85.1% yield, 95.83% purity) as a white solid.

Compounds 13-18

Compounds 13-18 were synthesized from Intermediate 11 and selected thiols or amines, using an experimental procedure analogous to the one used for obtaining Compound 12.

| Cpd | Structure | Intermediate | Reagent | Yield (%) |
|---|---|---|---|---|
| 13 | (structure) | 11 | (structure) | 37.0 |
| 14 | (structure) | 11 | (structure) | 28.9 |

-continued

| Cpd | Structure | Intermediate | Reagent | Yield (%) |
|---|---|---|---|---|
| 15 | 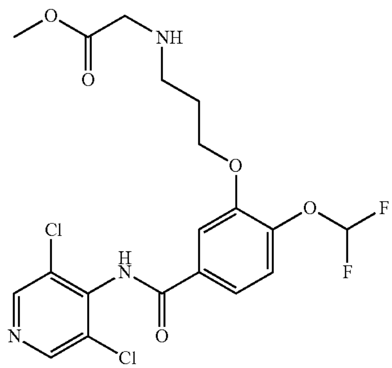 [SMILES: COC(=O)CNCCCOc1cc(C(=O)Nc2c(Cl)cncc2Cl)ccc1OC(F)F] | 11 | | 20.0 |
| 16 | 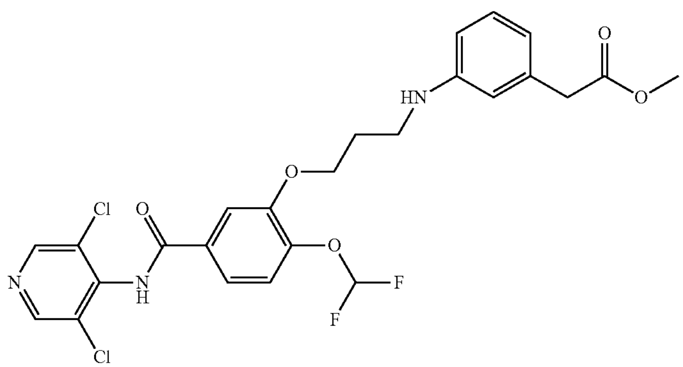 [SMILES: COC(=O)Cc1cccc(NCCCOc2cc(C(=O)Nc3c(Cl)cncc3Cl)ccc2OC(F)F)c1] | 11 | | 19.3 |
| 17 | 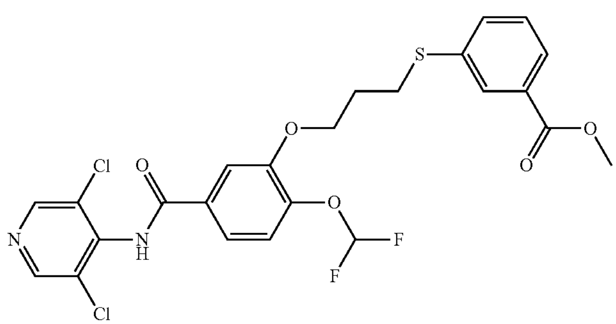 [SMILES: COC(=O)c1cccc(SCCCOc2cc(C(=O)Nc3c(Cl)cncc3Cl)ccc2OC(F)F)c1] | 11 | | 51.0 |
| 18 | 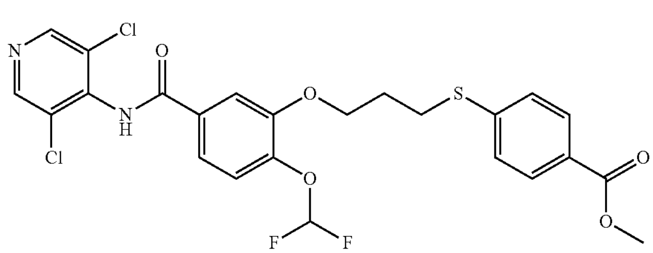 [SMILES: COC(=O)c1ccc(SCCCOc2cc(C(=O)Nc3c(Cl)cncc3Cl)ccc2OC(F)F)cc1] | 11 | | 59.5 |

Compound 19

2-hydroxyethyl (3-(5-((3,5-dichloropyridin-4-yl)carbamoyl)-2-(difluoromethoxy)phenoxy)propyl)carbamate

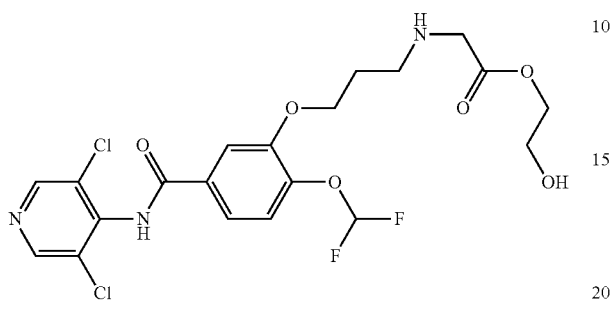

A mixture of Intermediate 12 (300 mg, 0.648 mmol, 1.0 eq), (Boc)$_2$O (170.2 mg, 0.78 mmol, 1.2 eq) and TEA (131 mg, 1.3 mmol, 2 eq) in DCM (10 ml) was stirred at room temperature for 16 hrs and the solvent was evaporated under reduced pressure, to afford the Boc-protected intermediate which was used for the next step without purification.

To a solution of this intermediate (150 mg, 0.26 mmol, 1.0 eq), ethylene glycol (80.7 mg, 1.3 mmol, 5.0 eq) and triethylamine (78.9 mg, 0.78 mmol, 3.0 eq) in DMF (4 ml) were added EDCl (40.4 mg, 0.26 mmol, 1.0 eq) and HOBT (19.9 mg, 0.13 mmol, 0.5 eq). The reaction mixture was stirred at 30° C. overnight and the solvent was evaporated under reduced pressure to give the crude Boc-protected ester.

The crude product was dissolved in a solution of TFA in DCM (4 ml, TFA/DCM 1:4) and the reaction mixture was stirred at 30° C. for 4 hrs. After solvent removal under reduced pressure, the crude product was purified by preparartive HPLC to give Compound 19 (32 mg, 24% yield).

Compound 20

2-(dimethylamino)ethyl (3-(5-((3,5-dichloropyridin-4-yl)carbamoyl)-2-(difluoromethoxy)phenoxy)propyl)carbamate

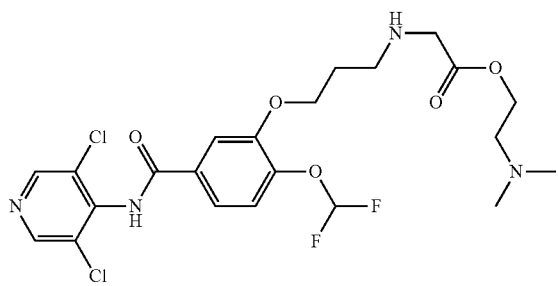 [SMILES: CN(C)CCOC(=O)CNCCCOc1cc(C(=O)Nc2c(Cl)cncc2Cl)ccc1OC(F)F]

Compound 20 was obtained from intermediate 12 (0.6 g, 1.7 mmol, 1.0 eq) and 2-(dimethylamino)ethanol (1.3 mmol, 5.0 eq), using an experimental procedure analogous to the one used for obtaining Compound 19 (35 mg, 25% yield).

Compound 21

Methyl 4-(5-((3,5-dichloropyridin-4-yl)carbamoyl)-2-(difluoromethoxy)phenoxy)benzoate

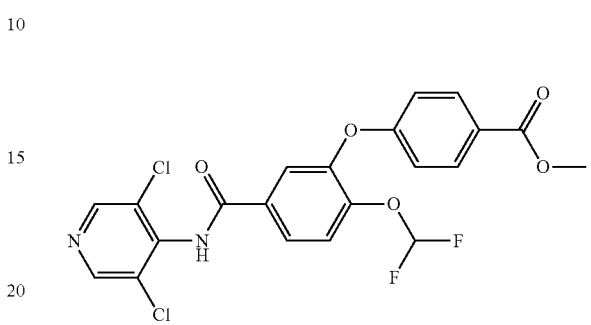

Compound 21 was obtained from Intermediate 16 (0.5 g, 1.5 mmol, 1.0 eq) and 3,5-dichloropyridin-4-amine (0.32 g, 1.9 mmol, 1.3 eq), using an experimental procedure analogous to the one used for obtaining Intermediate 7 (0.5 g, 70% yield).

Compound 22

Ethyl 3-(5-((3,5-dichloropyridin-4-yl)carbamoyl)-2-(difluoromethoxy)phenoxy)benzoate

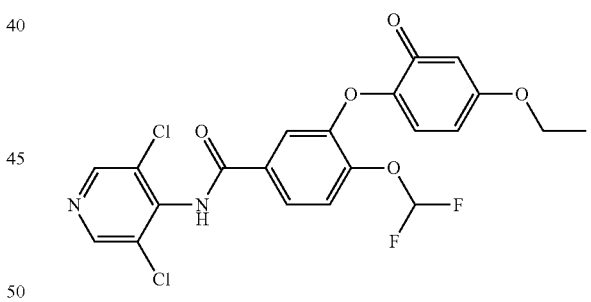

Compound 22 was obtained from intermediate 19 (0.6 g, 1.7 mmol, 1.0 eq) and 3,5-dichloropyridin-4-amine (0.36 g, 2.2 mmol, 1.3 eq), using an experimental procedure analogous to the one used for obtaining intermediate 7 (0.5 g, 59% yield).

Compounds 23-31

Yet additional compounds of the invention can be obtained by hydrolyzing the methyl/ethyl ester of compounds 15-18/21-22 and reacting the resulting acid with selected alcohols, using a procedure analogous to the one used for the synthesis of compounds 2-9.

| Cpd | Structure | Intermediate | Reagent | Yield (%) |
|---|---|---|---|---|
| 23 | 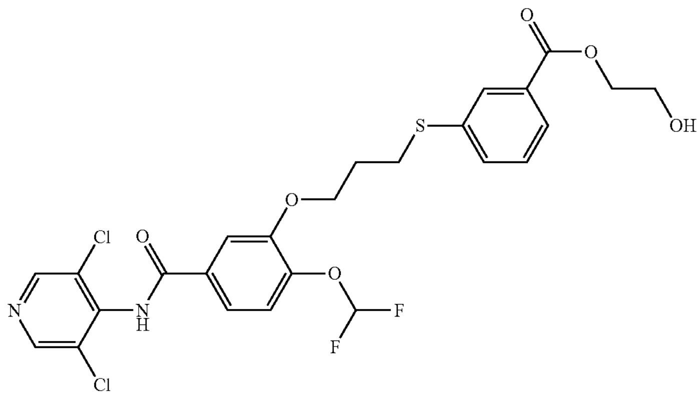 [SMILES: O=C(Nc1c(Cl)cncc1Cl)c1ccc(OC(F)F)c(OCCCSc2cccc(C(=O)OCCO)c2)c1] | 13 | HOCH₂CH₂OH | 18.6 |
| 24 | 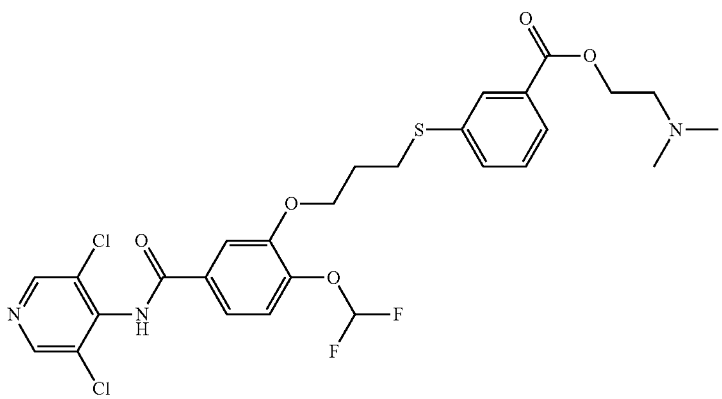 [SMILES: CN(C)CCOC(=O)c1cccc(SCCCOc2cc(C(=O)Nc3c(Cl)cncc3Cl)ccc2OC(F)F)c1] | 13 | HOCH₂CH₂N(CH₃)₂ | 18.5 |
| 25 | 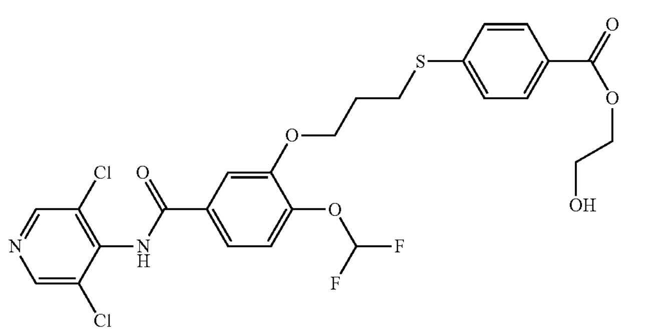 [SMILES: O=C(Nc1c(Cl)cncc1Cl)c1ccc(OC(F)F)c(OCCCSc2ccc(C(=O)OCCO)cc2)c1] | 14 | HOCH₂CH₂OH | 18.6 |
| 26 | 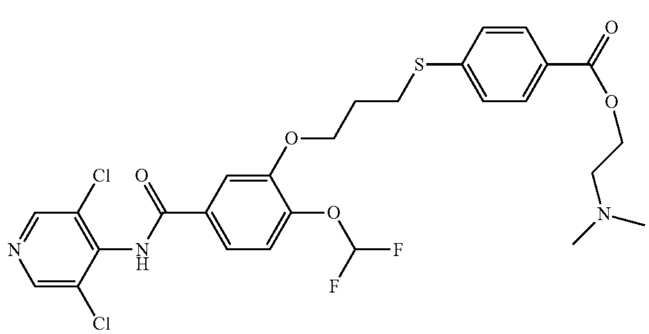 [SMILES: CN(C)CCOC(=O)c1ccc(SCCCOc2cc(C(=O)Nc3c(Cl)cncc3Cl)ccc2OC(F)F)cc1] | 14 | HOCH₂CH₂N(CH₃)₂ | 18.5 |

-continued

| Cpd | Structure | Intermediate | Reagent | Yield (%) |
|---|---|---|---|---|
| 27 | 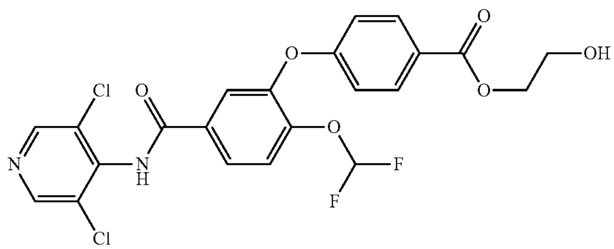 | 17 | HOCH₂CH₂OH | 10.0 |
| 28 | 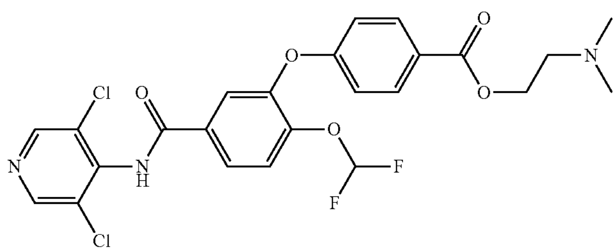 [SMILES: CN(C)CCOC(=O)c1ccc(Oc2cc(C(=O)Nc3c(Cl)cncc3Cl)ccc2OC(F)F)cc1] | 17 | HOCH₂CH₂N(CH₃)₂ | 23.0 |
| 29 | 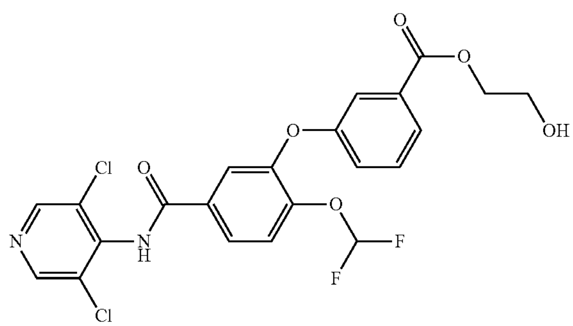 [SMILES: O=C(Nc1c(Cl)cncc1Cl)c1ccc(OC(F)F)c(Oc2cccc(C(=O)OCCO)c2)c1] | 20 | HOCH₂CH₂OH | 20 |
| 30 | 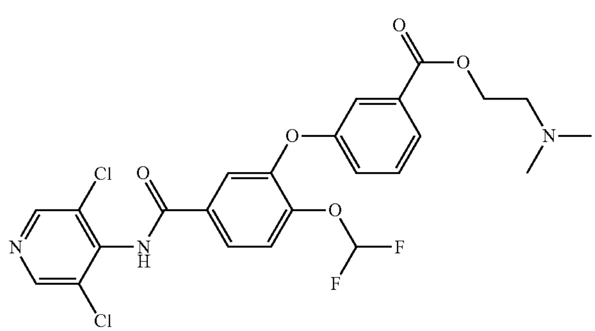 [SMILES: CN(C)CCOC(=O)c1cccc(Oc2cc(C(=O)Nc3c(Cl)cncc3Cl)ccc2OC(F)F)c1] | 20 | HOCH₂CH₂N(CH₃)₂ | 24 |
| 31 | 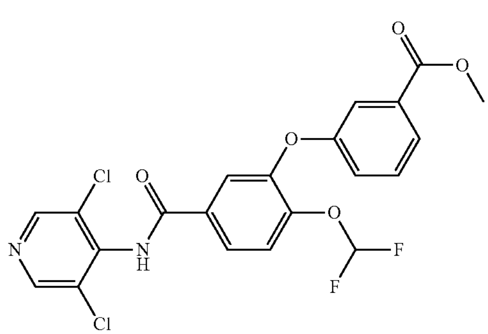 [SMILES: COC(=O)c1cccc(Oc2cc(C(=O)Nc3c(Cl)cncc3Cl)ccc2OC(F)F)c1] | 20 | MeOH | 26 |

B.2.2 Compounds of the Invention: N-Oxides

The corresponding N-oxides can be synthesized using an experimental procedure analogous to the one used for obtaining the compounds described above, by replacing 4-amino-3,5-dichloropyridine with 4-amino-3,5-dichloropyridine-N-oxide in the corresponding reaction step.

B.3. Metabolites Resulting from Compound Hydrolysis by Carboxylic Ester Hydrolases As indicated by formula I hereinabove, compounds of the invention contain an ester or cyclic ester (lactone) moiety. A number of metabolites resulting from hydrolysis of compounds of the invention by carboxylic ester hydrolases (EC3.1.1) can therefore be predicted.

In several cases, such metabolites correspond to intermediates used for synthesizing compounds of the invention; e.g. intermediate 12 represents the expected metabolite resulting from hydrolysis of compounds 15, 22 or 23. In other cases, the metabolite resulting from compound hydrolysis by carboxylic ester hydrolases can be chemically synthesized via hydrolysis of the parent compound by LiOH; as described hereinabove for the synthesis of several intermediates.

The following metabolites of compounds of the invention were synthesized for comparison purposes.

| Metabolite ID | Metabolite structure | Parent compound |
| --- | --- | --- |
| Met 1 | | Cpd 11 |
| Met 2 | | Cpd 14 |
| Met 3 | | Cpd 15 |

C. In Vitro Assays

C.1. PDE4 Inhibitory Activity Screening

The inhibitory activity of compounds of the present invention was evaluated in a biochemical assay, using a protocol adapted from Saldou et al, as described in Cell signal., 10 (1998), p 427-440. Various concentrations of the test compounds were incubated with recombinant PDE4B1 or PDE4D2 (isolated from Sf9 cells), using 40 nM cAMP as enzyme substrate. Incubation time was set to 30 minutes. The reaction was carried out at room temperature. At the end of the incubation time, residual cAMP concentration was determined, using HTRF as detection method.

Observed enzymatic activity was expressed as a percent of control specific activity ((measured specific activity/control specific activity)×100) obtained in the presence of the test compounds.

The $IC_{50}$ values (concentration causing a half-maximal inhibition of control specific activity) and Hill coefficients (nH) were determined by non-linear regression analysis of the inhibition curves generated with mean replicate values using Hill equation curve fitting (Y=D+[(A−D)/(1+(C/C50)nH)], where Y=specific activity, D=minimum specific activity, A=maximum specific activity, C=compound concentration, C50=$IC_{50}$ and nH=slope factor).

When evaluated under such conditions, compounds of the invention display an inhibitory concentration 50 ($IC_{50}$) that is <500 nM against PDE4B1 and/or PDE4D2. Preferred compounds display $IC_{50}$<100 nM. Most preferred compounds display $IC_{50}$<10 nM.

$IC_{50}$ Data for selected compounds:

| # Cpd | $IC_{50}$ (PDE4B1) | $IC_{50}$ (PDE4D2) |
|---|---|---|
| 1 | ++ | ++ |
| 2 | ++ | ++ |
| 3 | ++ | + |
| 4 | ++ | + |
| 5 | +++ | +++ |
| 6 | +++ | ++ |
| 7 | +++ | ++ |
| 8 | +++ | ++ |
| 9 | ++ | ++ |
| 10 | +++ | +++ |
| 11 | +++ | +++ |
| 12 | +++ | +++ |
| 13 | +++ | +++ |
| 14 | +++ | ++ |
| 15 | ++ | ++ |
| 16 | +++ | ++ |
| 17 | + | + |
| 18 | + | + |
| 19 | + | − |
| 21 | ++ | − |
| 22 | ++ | + |
| 23 | ++ | ++ |
| 24 | ++ | ++ |
| 25 | ++ | ++ |
| 26 | ++ | +++ |
| 27 | ++ | ++ |
| 28 | ++ | + |
| 29 | +++ | ++ |
| 30 | +++ | ++ |
| Met1 | + | + |
| Met2 | − | − |
| Met3 | − | − |
| Roflumilast | +++ | +++ |
| Rolipram | ++ | + |

−: $IC_{50}$ ≥ 500 nM
+: 500 nM > $IC_{50}$ ≥ 100 nM
++: 100 nM > $IC_{50}$ ≥ 10 nM
+++: 10 nM > $IC_{50}$
ND: Not determined yet.

C.2. Pharmacological Characterization

C.2.1. Stability Assay in Human and Other Species Plasma

Compounds are incubated at a concentration of 1 μM in rat (mice/rabbit/dog/rabbit) or human plasma. Samples are taken at fixed time points and the remnant of compound is determined by LC-MS/MS after protein precipitation. Half life of the compound is expressed in minutes.

When evaluated under such conditions, compounds of the invention display a half-life in human plasma ($t_{1/2}$) that is inferior to 60 minutes. Preferred compounds display a half-life that is inferior to 15 minutes.

The following table discloses example data for selected compounds, in human plasma. Half-life of compounds ($t_{1/2}$) is expressed in minutes.

| # Cpd | $t_{1/2}$ |
|---|---|
| 2 | ++ |
| 3 | ++ |
| 5 | + |
| 6 | + |
| 7 | + |
| 8 | ++ |
| 9 | ++ |
| 10 | ++ |
| 11 | ++ |
| 12 | ++ |
| 13 | ++ |
| 14 | ++ |
| 15 | + |
| 16 | ++ |
| 24 | ++ |
| 26 | ++ |
| 28 | + |
| 30 | ++ |

+: 15 min < $t_{1/2}$ < 60 min
++: $t_{1/2}$ < 15 min

C.2.2. Stability Towards Drug Metabolizing Enzymes in Lung S9

A 1 μM solution of the compounds is incubated with a reaction mixture containing lung S9 (from smokers) as well as the cofactors NADPH, UDPGA, PAPS and GSH. Samples are collected at 0, 15, 30 and 60 minutes post incubation. Negative control samples incubated with PKC inhibitors and S9 fraction in the absence of cofactors are run in parallel. By using LC-MS/MS analysis, the percent of compounds remaining at each time point, the metabolic half-life of the compounds (expressed in minutes) and the metabolic half-life of the control compounds are determined.

When evaluated under such conditions, compounds of the invention display a half-life on human lungS9 ($t_{1/2}$) that is superior to 60 minutes. The following table discloses example data for selected compounds. Half-life of compounds ($t_{1/2}$) is expressed in minutes.

| # Cpd | $t_{1/2}$ |
|---|---|
| 11 | >60 |
| 12 | >60 |
| 14 | >60 |

C.2.3. Stability Assay in Aqueous Humor

Compounds are incubated at a concentration of 1 µM in human or animal (e.g. rabbit) aqueous humor (AH). Samples are taken at fixed time points and the remnant of compound is determined by LC-MS/MS after protein precipitation.

When evaluated under such conditions, compounds of the invention display a half-life aqueous humor ($t_{1/2}$) that is superior to 60 minutes. The following table discloses example data for selected compounds evaluated in rabbit aqueous humor. Half-life of compounds ($t_{1/2}$) is expressed in minutes.

| # Cpd | $t_{1/2}$ |
|---|---|
| 15 | + |
| 19 | ++ |
| 20 | ++ |
| 21 | ++ |
| 27 | ++ |
| 28 | + |

+: 60 min < $t_{1/2}$ < 120 min
++: $t_{1/2}$ > 120 min

C2.4. Solubility in Aqueous Solution

Using a 10 mM stock solution of each compound in 100% DMSO, dilutions were prepared to a theoretical concentration of 200 µM in both phosphate buffer saline (PBS), pH7.4 and in 100% DMSO (as reference). Solutions (triplicates) were incubated at room temperature for 24 h on a shaker at 100 rpm. The solutions were then centrifugated at 13000 rpm for 30 min and the supernatant was further diluted to 2 µM in methanol. The supernatant was then analyzed by LC-MSMS. The concentration of compound in PBS supernatant was determined by comparing the MS peak area with that of the reference solution in DMSO.

| # Cpd | Solubility |
|---|---|
| 1 | + |
| 2 | + |
| 3 | − |
| 4 | − |
| 5 | ++ |
| 7 | ++ |
| 8 | ++ |
| 9 | + |
| 10 | ++ |
| 11 | + |
| 12 | + |
| 13 | + |
| 14 | + |
| 15 | ++ |
| 16 | − |
| 17 | − |
| 20 | + |
| 21 | + |
| 32 | + |
| 33 | ++ |
| 34 | + |
| 35 | + |
| Roflumilast | − |

−: Solubility < 10 µM
+: 10 µM ≤ Solubility < 100 µM
++: 100 µM ≤ Solubility

C.2.5 Membrane Permeability

The capacity of compounds of the invention to cross a lipophilic membrane was evaluated in a Pampa assay, using an assay plate containing structured layers of phospholipids supported on a PVDF filter (Benton Dickinson). In addition to test compounds, Propranolol, Atenolol and Reserpine were as reference compounds with very high, low and very low permeability, respectively. Each compound was tested in triplicate and was prepared as a 10 µM solution in 10 mM PBS pH=7.4 buffer containing 2% DMSO. Compounds were dosed in the donor chamber of the assay plate and incubated for 5 hours, at room temperature. Additionally, an equilibrium solution plate containing 6 µM of test compound was prepared. Test compound concentration in donor and acceptor chamber and in the equilibrium plate was quantified using HPLC-MS/MS. The subsequently calculated permeability coefficients were reported as $P_{app}$.

The following table discloses permeability data for selected compounds and metabolites.

| Compound | $P_{app}$ (Pampa; $10^{-6}$ cm/s) |
|---|---|
| 7 | 9.2 |
| 8 | 7.5 |
| 9 | 3.0 |
| 10 | 3.7 |
| 11 | 5.0 |
| 12 | 2.5 |
| 13 | 6.6 |
| 14 | 7.3 |
| 15 | 5.6 |
| 27 | 2.3 |
| 28 | 7.9 |
| 29 | 5.1 |
| 30 | 5.3 |
| Met1 | 0.03 |
| Met2 | 0.02 |
| Met3 | 0.02 |
| Propranolol | 9.5 |
| Atenolol | 0.17 |
| Reserpine | 0.008 |

D. Soft PDE4 Inhibitors for Local Treatment of PDE4-Associated Diseases

As discussed hereinabove, many development programs of PDE4 inhibitors have been discontinued due to side effects. In particular, many dose-limiting side effects reflect an adverse interaction of the compound with PDE4 expressed in non-target tissues. Hence, systemic exposure to PDE4 inhibitors should preferably be avoided.

Soft drugs will solve the technical problem of providing sustained pharmacological activity in the target tissue or organ, while avoiding systemic PDE4 inhibition. In view the data disclosed in sections C1 and C2, it will be appreciated that compounds of the invention represent soft drugs. In particular, data demonstrates that:

C.1.1: Compounds of the invention are PDE4 inhibitors

C.2.1: Compounds of the invention are rapidly degraded in plasma and, by extension, in whole blood, thereby allowing reduced systemic exposure after topical administration.

C2.2 & C2.3: Compounds of the invention display good stability in potential target organs and fluids, such as lung or aqueous humor, thereby allowing sustained pharmacological activity after topical administration to target organs such as lung or eye.

C2.5: Compounds of the invention show good membrane permeability, allowing inhibition of the intracellular PDE4.

C1.1 and C2.5: The metabolites resulting from the hydrolysis of compounds of the invention by carboxylic ester hydrolases display reduced inhibitory potency against PDE4 and reduced membrane permeability.

The invention claimed is:

1. A compound of Formula I or a stereoisomer, tautomer, racemic, salt, hydrate, or solvate thereof,

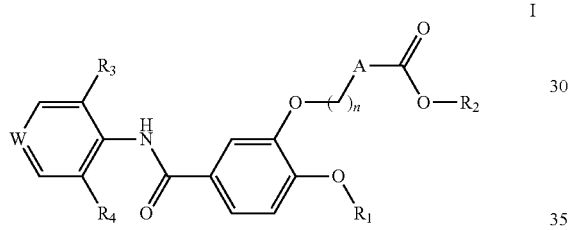

Wherein

W is N, N=O, or $N^+$—$O^-$;

A is selected from the group consisting of a direct bond, —Z—Y, —C(=O)—NH—$R_{21}$, —C(=O)—NH—$R_{21}$—Z—Y—, —N($R_{22}$)—$R_{23}$—, and —Z-Cy-$(CH_2)_m$—: wherein Z is selected from a direct bond, O, NH, and S;

$R_{21}$ is a direct bond or an optionally substituted $C_{1-8}$alkylene;

$R_{22}$ is selected from hydrogen and $C_{1-8}$ alkyl;

$R_{23}$ is an optionally substituted $C_{1-8}$alkylene;

Cy is an optionally substituted cyclic structure selected from cycloalkyl, aryl, or heteroaryl; and m is selected from 0 and 1;

$R_1$ is selected from cycloalkyl or optionally substituted alkyl;

$R_2$ is an optionally substituted group selected from $C_{1-8}$alkyl, $C_{3-8}$cycloalkyl, heterocyclyl, aryl, and heteroaryl; with the proviso that if Y is part of A then $R_2$ together with Y forms a cyclic ester (lactone) structure selected from

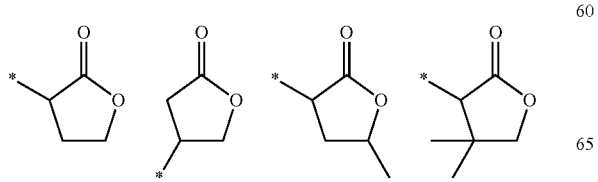

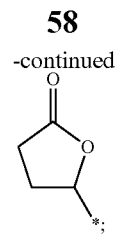

$R_3$ and $R_4$ are independently selected from hydrogen, $C_{1-8}$alkyl, or halo;

n is an integer from 0 to 9.

2. The compound according to claim 1, wherein

W is N, N=O, or $N^+$—$O^-$;

A is selected from the group consisting of a direct bond, —Z—Y, —C(=O)—NH—$R_{21}$, —C(=O)—NH—$R_{21}$—Z—Y—, —N($R_{22}$)—$R_{23}$—, and —Z-Cy-$(CH_2)_m$—; wherein Z is selected from a direct bond, O, NH, and S;

$R_{21}$ is a direct bond or an optionally substituted $C_{1-8}$alkylene;

$R_{22}$ is selected from hydrogen and $C_{1-8}$ alkyl;

$R_{23}$ is an optionally substituted $C_{1-8}$alkylene;

Cy is an optionally substituted cyclic structure selected from cycloalkyl, aryl, or heteroaryl; and m is selected from 0 and 1;

$R_1$ is selected from cycloalkyl or optionally substituted alkyl;

$R_2$ is an optionally substituted group selected from $C_{1-8}$alkyl, $C_{3-8}$cycloalkyl, heterocyclyl, aryl, and heteroaryl; with the proviso that if Y is part of A then $R_2$ together with Y forms a cyclic ester (lactone) structure selected from

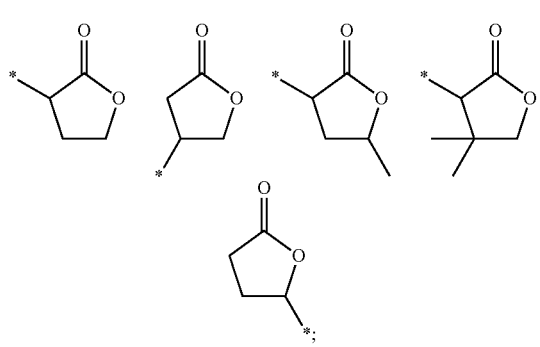

$R_3$ and $R_4$ are independently selected from hydrogen, $C_{1-8}$alkyl, or halo; n is an integer from 0 to 9.

3. The compound according to claim 1, wherein $R_2$ is selected from $C_{1-8}$alkyl, $C_{3-8}$cycloalkyl, heterocyclyl, aryl, and heteroaryl; wherein said $C_{1-8}$alkyl, $C_{3-8}$cycloalkyl, heterocyclyl, aryl, and heteroaryl is optionally substituted with halo, hydroxyl, nitro, amino, cyano, alkyl, alkenyl, alkynyl, alkoxy, —S-alkyl, alkylamino, dialkylamino, aryl, heteroaryl, cycloalkyl, and heterocyclyl;

with the proviso that if Y is part of A then $R_2$ together with Y forms a cyclic ester (lactone) structure selected from

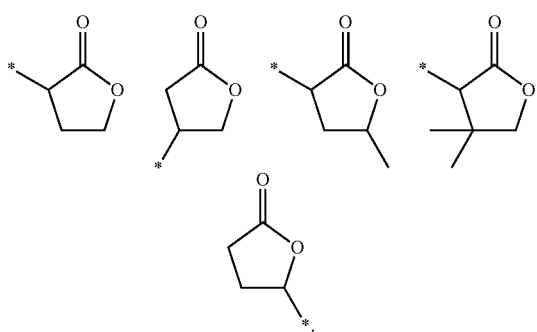

4. The compound according to claim 1, wherein
R$_2$ is C$_{1-8}$alkyl or aryl; wherein
said C$_{1-8}$alkyl is optionally substituted with a substituent selected from the group consisting of aryl, heterocyclyl, alkoxy, dialkylamino, and hydroxyl; and
said aryl is optionally substituted with halo;
with the proviso that if Y is part of A then R$_2$ together with Y forms a cyclic ester (lactone) structure selected from

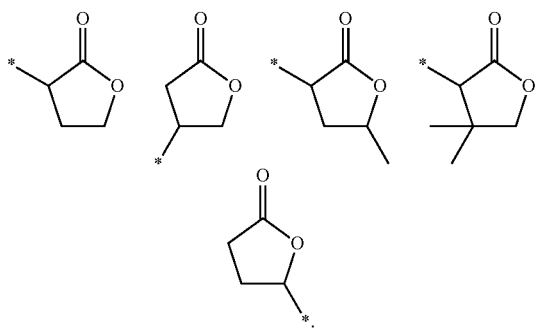

5. A pharmaceutical composition comprising a compound as defined in claim 1 and at least one pharmaceutically acceptable carrier, diluent, excipient, or adjuvant.

6. A method for inhibiting PDE4, comprising:
administering to a subject in need thereof a therapeutic effective amount of a compound as defined in claim 1.

7. A method for treating at least one disease or disorder selected from the group consisting of immunological disorders, fibrotic diseases, and inflammatory diseases, comprising:
administering to a subject in need thereof a therapeutic effective amount of a compound as defined in claim 1.

8. A method for treating at least one disease or disorder selected from the group consisting of idiopathic pulmonary fibrosis, inflammatory eye diseases, inflammatory airway diseases, skin diseases, and intestinal diseases, comprising
administering to a subject in need thereof a therapeutic effective amount of a compound as defined in claim 1.

9. The method according to claim 8 wherein at least one disease is an inflammatory eye disease.

10. The method according to claim 9 wherein said inflammatory eye disease is selected from dry eye disease or allergic eye disease.

11. The method according to claim 8 wherein said at least one disease is an inflammatory airway disease.

12. The method according to claim 11 wherein said inflammatory airway disease is selected from asthma or chronic obstructive pulmonary disease.

13. The method according to claim 8 wherein said at least one disease is a skin disease.

14. The method according to claim 13 wherein said skin disease is selected from atopic dermatitis or psoriasis.

15. The method according to claim 8 wherein said at least one disease is an intestinal disease.

16. The method according to claim 15, wherein said intestinal disease is inflammatory bowel disease.

* * * * *